United States Patent
Ciechanover et al.

(10) Patent No.: US 12,421,510 B2
(45) Date of Patent: Sep. 23, 2025

(54) PEPTIDE, A COMPLEX AND A METHOD FOR TREATING CANCER

(71) Applicant: TECHNION RESEARCH & DEVELOPMENT FOUNDATION LIMITED, Haifa (IL)

(72) Inventors: Aaron Ciechanover, Caesarea (IL); Yelena Kravtsova, Haifa (IL); Gilad Goldhirsh, Kfar Saba (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 1084 days.

(21) Appl. No.: 17/284,966

(22) PCT Filed: Nov. 27, 2019

(86) PCT No.: PCT/IL2019/051294
§ 371 (c)(1),
(2) Date: Apr. 13, 2021

(87) PCT Pub. No.: WO2020/110114
PCT Pub. Date: Jun. 4, 2020

(65) Prior Publication Data
US 2021/0348152 A1    Nov. 11, 2021

Related U.S. Application Data

(60) Provisional application No. 62/772,892, filed on Nov. 29, 2018.

(51) Int. Cl.
C12N 9/00     (2006.01)
A61K 38/00    (2006.01)
A61K 47/64    (2017.01)
A61P 35/00    (2006.01)

(52) U.S. Cl.
CPC ............... *C12N 9/93* (2013.01); *A61K 47/64* (2017.08); *A61P 35/00* (2018.01); *A61K 38/00* (2013.01)

(58) Field of Classification Search
None
See application file for complete search history.

(56) References Cited

U.S. PATENT DOCUMENTS 4,683,195 A    7/1987  Mullis et al.

FOREIGN PATENT DOCUMENTS

CN    1403478 A       3/2003
WO    2016116922      7/2016

OTHER PUBLICATIONS

NCBI Reference Sequence: XP_010222884.1 Nov. 13, 2014. (downloaded on Aug. 19, 2024) E3 ubiquitin-protein ligase RNF123 [Tinamus guttatus] (Year: 2014).*

(Continued)

*Primary Examiner* — Anand U Desai
(74) *Attorney, Agent, or Firm* — The Roy Gross Law Firm, LLC; Roy D. Gross

(57) ABSTRACT

A peptide comprising the amino acid sequence set forth in WILVRLW (SEQ ID NO: 1), or any functionally related variant thereof, a complex, conjugate or chimera comprising the same, wherein the peptide is linked with or without a linker to RING or to a molecule or peptide that recruits E3 ligase and method for treating cancer by administering the same.

19 Claims, 13 Drawing Sheets

Specification includes a Sequence Listing.

(56) References Cited

OTHER PUBLICATIONS

PDF sequence search results H701117—UniProt 051169; database date Feb. 13, 1998; downloaded Feb. 7, 2025 (Year: 1998).*

PDF sequence search result XP_013889121.1; database date Feb. 28, 2018; downloaded Feb. 7, 2025 (Year: 2018).*

Kamura et al (2004) Cytoplasmic ubiquitin ligase Kip1 regulates proteolysis of p27 Kip1 at G1 phase, Nature Cell Biology 6(12):1229-1235. DOI: 10.1038/ncb1194.

Glickman et al (2002). The Ubiquitin-proteasome proteolytic pathway: destruction for the sake of construction. Physiol. Rev. 82, 373-428.

Kravtsova et al (2015). KPC1-mediated ubiquitination and proteasomal processing of NFkB1 p105 to p50 restricts tumor growth. Cell 161, 333-347.

Booth et al.(1988). The use of a 'universal'yeast expression vector to produce an antigenic protein of *Mycobacterium leprae*. Immunology letters, 19(1), 65-69.

Bowie et al (1990). Deciphering the message in protein sequences: tolerance to amino acid substitutions. Science, 247(4948), 1306-1310.

Abraham et al (2007). Nucleobase analogs for degenerate hybridization devised through conformational pairing analysis. BioTechniques, 43(5), 617-624.

Caruther (1985). Gene synthesis machines: DNA chemistry and its uses. Science, 230(4723), 281-285.

Zoller et al (1982). Oligonucleotide-directed mutagenesis using M13-derived vectors: an efficient and general procedure for the production of point mutations in any fragment of DNA. Nucleic Acids Research, 10(20), 6487-6500.

Saiki et al (1988). Primer-directed enzymatic amplification of DNA with a thermostable DNA polymerase. Science, 239(4839), 487-491.

Gardella et al. (1990). Expression of human parathyroid hormone-(1-84) in *Escherichia coli* as a factor X-cleavable fusion protein. Journal of Biological Chemistry, 265(26), 15854-15859.

International Search Report of PCT/IL2019/051294 Completed Dec. 31, 2019; mailed Dec. 31, 2019 4 pages.

Written Opinion of PCT/IL2019/051294 Completed Dec. 31, 2019; mailed Dec. 31, 2019 5 pages.

* cited by examiner (i)

(ii)

PEPTIDE, A COMPLEX AND A METHOD FOR TREATING CANCER

CROSS REFERENCE TO RELATED APPLICATIONS

This application is a National Phase of PCT Patent Application No. PCT/IL2019/051294 having International filing date of Nov. 27, 2019, which claims the benefit of priority of U.S. Provisional Patent Application No. 62/772,892, filed Nov. 29, 2018, the contents of which are all incorporated herein by reference in their entirety.

BACKGROUND OF THE INVENTION

Ubiquitin modification of target proteins can alter their stability, localization, or function, and as a result, plays fundamental roles in maintaining the cellular steady state and quality control. An important function of the system is the degradation of the ubiquitin-tagged substrates by the 26S proteasome (Glickman and Ciechanover, 2002). One important group of substrates of the ubiquitin-proteasome system (UPS) is the NF-κB family of eukaryotic transcription factors.

NF-κB is a central mediator of the immune and inflammatory responses, and consequently, plays an important role in the pathogenesis of malignancies. The activation of NF-κB is mediated by a multistep, complex cascade that is regulated by different modes of ubiquitination, involving both proteolytic and non-proteolytic steps. One critical reaction is the processing of the inactive long protein precursor NF-κB1 p105 to the shorter p50 active subunit of transcriptional regulator. Processing is a rare event in proteasomal proteolysis of the numerous known substrates of the ubiquitin system, most of which are completely destroyed. A recent study identified the ubiquitin ligase KPC1 (KIP1 Ubiquitination Promoting Complex; RNF123) as the ligase that mediates ubiquitination and proteasomal processing of NF-κB1 p105 to p50. Importantly, the generation of p50 by KPC1 results in a strong tumor suppressive effect (Kravtsova-Ivantsiv et al., 2015). KPC1 was also shown to degrade the cyclin-dependent kinase inhibitor p27Kip1 in the G1 phase of the cell cycle.

KPC1 was identified as the Ub ligase (E3) that binds to the ankyrin repeats domain of p105, ubiquitinates it, and mediates its processing to p50. Importantly, overexpression of either KPC1 or p50 inhibits tumor growth. Also, an overabundance of p50 downregulates p65, suggesting that a p50·p50 homodimer may modulate transcription in place of the tumorigenic p50·p65 heterodimer. Transcript analysis reveals increased expression of genes associated with tumor-suppressive signals.

The mechanism of action of KPC1 in binding p105, which leads to its processing remains unknown. Further, the area in KPC1 that serves to bind p105 has remained elusive (Kravtsova-Ivantsiv et al., 2015). Therefore, there is a need to identify this linkage in order to develop tumor suppressive drugs.

SUMMARY OF THE INVENTION

In the current invention, the inventors identified, in cellulo, that KPC1 interacts with p105 through seven amino acids, WILVRLW (SEQ ID. No. 1), which comprise positions 968-974 in the sequence of the KPC1 protein.

Embodiments of the invention are directed to a peptide comprising the amino acid sequence set forth in WILVRLW (SEQ ID NO: 1), or any functionally related variant thereof. Embodiments of the invention are directed to a peptide consisting essentially of an amino acid sequence set forth in WILVRLW (SEQ ID NO: 1), or any functionally related variant thereof.

Further embodiments are directed to a peptide comprising the amino acid sequence set forth in WILVRLW (SEQ ID NO: 1), or any functionally related variant thereof, wherein the peptide includes 7-20 amino acids. Further embodiments are directed to a peptide comprising the amino acid sequence set forth in WILVRLW (SEQ to less than 20, 40, 60, 80, 100, 120, 140, 160, 180, 200, 220, 240, 260, 280, or 300 amino acids. Such a peptide interacts with p105.

Further embodiments are directed to a peptide comprising the amino acid sequence set forth in WILVRLW (SEQ ID NO: 1), or any functionally related variant thereof, wherein the peptide includes 7-20 amino acids. Such a peptide interacts with p105.

Further embodiments of the invention are directed to a peptide having at least 75, 76, 77, 78, 79, 80, 81, 82, 83, 84, 85, 86, 87, 88, 89, 90, 91, 92, 93, 94, 95, 96, 97, 98, 99% homology to such a peptide, as disclosed herein. Such a peptide interacts with p105.

According to some embodiments, the sequence of the KPC1 protein is set forth in SEQ ID NO: 2, which is as follows:

```
MASKGAGMSF SRKSYRLTSD AEKSRVTGIV QEKLLNDYLN

RIFSSSEHAP PAATSRKPLN FQNLPEHLDQ LLQVDNEEEE

SQGQVEGRLG PSTVVLDHTG GFEGLLLVDD DLLGVIGHSN

FGTIRSTTCV YKGKWLYEVL ISSQGLMQIG WCTISCRFNQ

EEGVGDTHNS YAYDGNRVRK WNVTTTNYGK AWAAGDIVSC

LIDLDDGTLS FCLNGVSLGT AFENLSRGLG MAYFPAISLS

FKESVAFNFG SRPLRYPVAG YRPLQDPPSA DLVRAQRLLG

CFRAVLSVEL DPVEGRLLDK ESSKWRLRGQ PTVLLTLAHI

FHHFAPLLRK VYLVEAVLMS FLLGIVEKGT PTQAQSVVHQ

VLDLLWLFME DYEVQDCLKQ LMMSLLRLYR FSPIVPDLGL

QIHYLRLTIA ILRHEKSRKF LLSNVLFDVL RSVVFFYIKS

PLRVEEAGLQ ELIPTTWWPH CSSREGKEST EMKEETAEER

LRRRAYERGC QRLRKRIEVV EELQVQILKL LLDNKDDNGG

EASRYIFLTK FRKFLQENAS GRGNMPMLCP PEYMVCFLHR

LISALRYYWD EYKASNPHAS FSEEAYIPPQ VFYNGKVDYF

DLQRLGGLLS HLRKTLKDDL ASKANIVIDP LELQSTAMDD

LDEDEEPAPA MAQRPMQALA VGGPLPLPRP GWLSSPTLGR

ANRFLSTAAV SLMTPRRPLS TSEKVKVRTL SVEQRTREDI

EGSHWNEGLL LGRPPEEPEQ PLTENSLLEV LDGAVMMYNL

SVHQQLGKMV GVSDDVNEYA MALRDTEDKL RRCPKRRKDI

LAELTKSQKV FSEKLDHLSR RLAWVHATVY SQEKMLDIYW

LLRVCLRTIE HGDRTGSLFA FMPEFYLSVA INSYSALKNY

FGPVHSMEEL PGYEETLTRL AAILAKHFAD ARIVGTDIRD

SLMQALASYV CYPHSLRAVE RIPEEQRIAM VRNLLAPYEQ
```

-continued

```
RPWAQTNWIL VRLWRGCGFG YRYTRLPHLL KTKLEDANLP

SLQKPCPSTL LQQHMADLLQ QGPDVAPSFL NSVLNQLNWA

FSEFIGMIQE IQQAAERLER NFVDSRQLKV CATCFDLSVS

LLRVLEMTIT LVPEIFLDWT RPTSEMLLRR LAQLLNQVLN
RVTAERNLFD RVVTLRLPGL ESVDHYPILV AVTGILVQLL
VRGPASEREQ ATSVLLADPC FQLRSICYLL GQPEPPAPGT
ALPAPDRKRF SLQSYADYIS ADELAQVEQM LAHLTSASAQ
AAAASLPTSE EDLCPICYAH PISAVFQPCG HKSCKACINQ
HLMNNKDCFF CKTTIVSVED WEKGANTSTT SSAA
```

Further embodiments of the invention are directed to a complex, or a chimera, or a conjugate (all of which may be used interchangeably) that is optionally a polypeptide comprising a peptide comprising the amino acid sequence set forth in WILVRLW (SEQ ID NO: 1), or any functionally related variant thereof, or to a peptide having at least 75, 76, 77, 78, 79, 80, 81, 82, 83, 84, 85, 86, 87, 88, 89, 90, 91, 92, 93, 94, 95, 96, 97, 98, 99% homology to the amino acid sequence set forth in WILVRLW (SEQ ID NO: 1), wherein the peptide is bound to a linker and wherein the linker is bound to RING.

In some embodiments of the invention, the RING (Really Interesting New Gene) is a RING domain which is a special type of zinc binding domain. The consensus RING sequence is $CX_2CX_{(9-39)}CX_{(1-3)}HX_{(2-3)}C/HX_2CX_{(4-48)}CX_2C$ with eight cysteines and histidines in a "cross-brace" topology to coordinate two zinc ions.

This protein domain contains in some embodiments of the invention from between about 40 to 60 amino acids.

In some embodiments of the invention, the RING is derived from KPC1. In some embodiments the RING contains the amino acid sequence of CPICYAHPISAVFQPCGHKSCKACINQHLMNNKDCFFC (SEQ ID. No. 4).

In some embodiments of the invention the linker may comprise between 2-300 amino acids. In some embodiments of the invention the linker may comprise between 2-10 amino acids. In some embodiments of the invention the linker may comprise between 2-50 amino acids. In some embodiments of the invention the linker may comprise between 2-100 amino acids. In some embodiments of the invention the linker may comprise between 2-200 amino acids. In some embodiments of the invention the linker may comprise between 2-8 amino acids. Further embodiments of the invention are directed to a functionally equivalent molecule that mimics a functional activity of the peptide disclosed herein in SEQ ID. No. 1, wherein the molecule is a peptidomimetic, a stapled peptide, or a chemical compound. This functionally equivalent molecule may replace the WILVRLW (SEQ ID NO: 1) in the above described complex that comprises a the RING and possibly a linker.

In some embodiments of the invention, the functionally equivalent molecule that mimics a functional activity of the peptide disclosed herein is SEQ ID. No. 1, wherein the molecule is a peptidomimetic, a stapled peptide or a chemical compound is conjugated with or without a linker to a small molecule that recruits E3 ligase or to a peptide that recruits E3 ligase.

Such a small molecule that recruits ubiquitin ligase (E3) may be, for example, lenalidomide or thalidomide, a proteolysis targeting chimera (PROTAC), or any fragment thereof that is capable of recruiting ubiquitin ligase (E3). According to some embodiments of the invention, there is provided a peptide comprising the amino acid sequence set forth in WILVRLW (SEQ ID NO: 1), or any functionally related variant thereof, or a peptide having at least 75, 76, 77, 78, 79, 80, 81, 82, 83, 84, 85, 86, 87, 88, 89, 90, 91, 92, 93, 94, 95, 96, 97, 98, 99% homology to the amino acid sequence set forth in WILVRLW (SEQ ID NO: 1), conjugated with or without a linker to a small molecule that recruits E3 ligase as described herein. Example to such molecule is provided below.

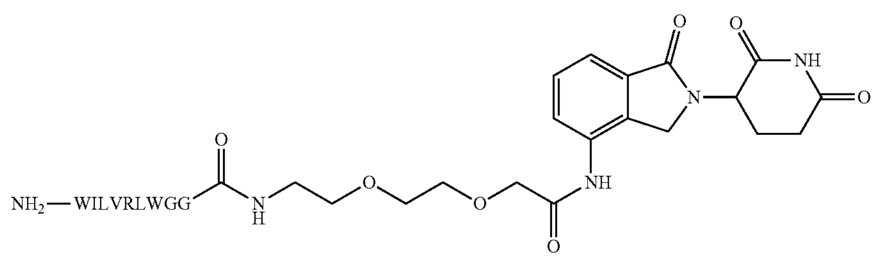

Such an exemplary chimera contains the peptide of SEQ ID NO: 1 connected to GG, which is connected to a small molecule derived from lenalidomide.

In some embodiments of the invention, there is provided a conjugate comprising the peptide of SEQ ID NO: 1 or functionally equivalent molecule thereof and a molecule or peptide that recruits E3 ligase.

Additional embodiments are directed to a pharmaceutical composition comprising a therapeutically effective amount of a peptide of SEQ ID. No. 1 as disclosed herein or a functionally equivalent molecule, as disclosed, and a pharmaceutically acceptable carrier or excipient. Additional embodiments are directed to a pharmaceutical composition comprising a therapeutically effective amount of a complex, a chimera or a conjugate (all of which are used here interchangeably) comprising the peptide of SEQ ID. No. 1 as disclosed herein or a functionally equivalent molecule, as disclosed, linked to a linker (as described above), which is linked to either a RING, or to PROTAC or any part thereof, which can recruit E3 ligase and a pharmaceutically acceptable carrier or excipient.

Embodiments of the invention are directed to an isolated polynucleotide encoding a peptide, any functionally related variant thereof or encoding the complex comprising the peptide, or any functionally related variant thereof, wherein the peptide is bound to a linker and the linker is bound to RING, as disclosed herein.

Further embodiments of the invention are directed to a plasmid or a vector comprising the isolated polynucleotide, as disclosed herein. Additional embodiments are directed to a pharmaceutical composition comprising a therapeutically effective amount of the polynucleotide disclosed herein and a pharmaceutically acceptable carrier or excipient.

Additional embodiments are directed to a vaccine comprising an effective amount of any of the complex molecule described herein, or a functionally equivalent molecule disclosed herein, and optionally an adjuvant. Further embodiments of the invention are directed to a vaccine comprising an effective amount of polynucleotide as disclosed herein, and optionally an adjuvant, which may be delivered to a mammal by any method such as, for example, by using a polymer based reagent used to deliver any nucleic acid to any animal such as, for example, JetPEI reagent.

In some embodiments of the invention, there is provided a method of treating cancer comprising the step of administering a therapeutically effective amount the complex described herein, thereby treating cancer.

In some embodiments of the invention, there is provided a method of suppressing tumor growth comprising the step of administering a therapeutically effective amount the complex described herein thereby suppressing tumor growth.

In some embodiments of the invention, there is provided a method of treating cancer comprising the step of administering a therapeutically effective amount of: a complex comprising a peptide comprising the amino acid sequence set forth in WILVRLW (SEQ ID NO: 1), or any functionally related variant thereof, wherein the peptide is linked to a linker and wherein the linker is linked to RING; or a conjugate comprising a peptide comprising the amino acid sequence set forth in WILVRLW (SEQ ID NO: 1), or of any of the functionally related variants thereof, linked with or without a linker, to a small molecule or a peptide that recruits E3 ligase; or a conjugate comprising a functionally equivalent molecule that mimics a functional activity of the peptide comprising the amino acid sequence set forth in WILVRLW (SEQ ID NO: 1), or of any of the functionally related variants thereof, wherein the molecule is a peptidomimetic, a stapled peptide, or a chemical compound, and wherein the functionally equivalent molecule is linked with or without a linker to a small molecule or a peptide that recruits E3 ligase thereby treating cancer.

In some embodiments, the cancer is breast cancer, bone osteosarcoma or glioblastoma.

In some embodiments, the tumor is a breast tumor, a bone tumor or a brain tumor.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A is a schematic representation of the KPC1 species used in the experiment shown in FIG. 1B. (i) Illustration of the domains of KPC1: SPRY, coiled coil (CC) and RING. (ii) KPC1Δ969-1314, that lacks amino acids 969-1314. (iii) KPC1Δ1-438 & 1039-1314 lacks the amino acids 1-438 and amino acids 1039-1314. (iv) KPC1Δ1-967 lacks amino acids 1-967. (v) KPC1Δ1-1042 lacks the amino acids 1-1042.

FIG. 1B is a western blot showing the following: HEK293T cells were transfected with cDNAs coding for p105-HA (lanes 1-6), along with the different KPC1 species as following: W.T KPC1 (lane 1), KPC1Δ969-1314 (lane 2), KPC1Δ1-438 & 1039-1314 (lane 3), KPC1Δ1-967 (lane 4) and KPC1Δ1-1042 (lane 5). Lane 6 was transfected with an empty vector. KPC1 species were immunoprecipitated using immobilized FLAG antibodies, resolved by SDS-page, and NF-κB1 and KPC1 proteins were visualized by anti-NF-κB1 (FIG. 1B (upper)) and anti-FLAG (FIG. 1B (bottom)) antibodies, respectively. 10% of the total cell lysate was analyzed for the expression of p105-HA.

FIG. 2A is a schematic representation of KPC1 species used in the experiment shown in FIG. 2B that was directed to evaluating the region of KPC1 that is responsible for the interaction with p105. (vi) Illustration of the domains of KPC1: SPRY, coiled coil (CC), RING and the region that is responsible for the interaction with p105. (vii) KPC1Δ967-1043, lacks the amino acids 967-1043. (viii) KPC1ΔCC domain, lacks the amino acids 1041-1061. (ix) KPC1Δ1-973, lacks the amino acids 1-973. (x) KPC1Δ1-1017, lacks the amino acids 1-1017.

FIG. 2B is a western blot. HEK293T cells were transfected with cDNAs coding for p105-HA (lanes 1-7), along with different KPC1 species as following: WT KPC1 (lane 1), KPC1Δ1-967 (lane 2), KPC1Δ967-1043 (lane 3), KPC1Δ1-973 (lane 4), KPC1Δ1-1017 (lane 5) and KPC1ΔCC domain (lane 6). Lane 7 represents cells that were transfected with empty vector. KPC1 species were immunoprecipitated using immobilized FLAG antibodies, resolved by SDS-page. NF-κB1 and KPC1 proteins were visualized with anti-NF-κB1 (FIG. 2B (i)) and anti-FLAG (FIG. 2B (ii)) antibodies, respectively. 10% of the total cell lysate was analyzed for the expression of p105-HA. FIG. 3A is a schematic representation of KPC1 species used in the experiment shown in FIG. 3B that was directed to evaluating the region of KPC1 that is responsible for the interaction with p105.

```
(xi) WILVRLW-KPC1 Δ 1-1253 i.e
                                          (SEQ ID NO: 8)
WILVRLWCPICYAHPISAVFQPCGHKSCKACINQHLMNNKDCFFCKTTIV

SVEDWEKGANTSTTSSAA,
lacks the amino acids 1-1253.

It contains at its N-terminus the amino acids
                                          (SEQ ID NO: 1)
WILVRLW.

(xii) ILVRLW-KPC1 Δ 1-1253, i.e
                                          (SEQ ID NO: 10)
ILVRLWCPICYAHPISAVFQPCGHKSCKACINQHLMNNKDCFFCKTTIVS VEDWEKGANTSTTSSAA
lacks the amino acids 1-1253.

Its N-terminus contains the amino acids
                                          (SEQ ID NO: 9)
ILVRLW.

(xiii) LVRLW-KPC1 Δ 1-1253, i.e.
                                          (SEQ ID NO: 11)
LVRLWCPICYAHPISAVFQPCGHKSCKACINQHLMNNKDCFFCKTTIVSV EDWEKGANTSTTSSAA
lacks the amino acids 1-1253.

Its N-terminus contains the amino acids
                                          (SEQ ID NO: 18)
LVRLW.
```

-continued (xiv) VRLW-KPC1 Δ 1-1253, lacks the amino
acids 1-1253. i.e
                                  (SEQ ID NO: 12)
VRLWCPICYAHPISAVFQPCGHKSCKACINQHLMNNKDCFFCKTTIVSVE

DWEKGANTSTTSSAA.

It contains at its N-terminus the amino acids
                                  (SEQ ID NO: 19)
VRLW.

(xv) RLW-KPC1 Δ 1-1253, i.e
                                  (SEQ ID NO: 13)
RLWCPICYAHPISAVFQPCGHKSCKACINQHLMNNKDCFFCKTTIVSVED

WEKGANTSTTSSAA
lacks the amino acids 1-1253.

It contains at its N-terminus the amino acids
RLW.

(xvi) KPC1 Δ 1-1253, lacks the amino acids
1-1253.

(xvii) WILVRL-KPC1 A 1-1253, lacks the
amino acids 1-1253 i.e.
                                  (SEQ ID NO: 14)
WILVRLCPICYAHPISAVFQPCGHKSCKACINQHLMNNKDCFFCKTTIVS

VEDWEKGANTSTTSSAA.

It contains at its N-terminus the amino acids
                                  (SEQ ID NO: 20)
WILVRL.

(xviii) WILVR-KPC1 Δ 1-1253, lacks the amino
acids 1-1253 i.e.
                                  (SEQ ID NO: 15)
WILVRCPICYAHPISAVFQPCGHKSCKACINQHLMNNKDCFFCKTTIVSV

EDWEKGANTSTTSSAA.

It contains at its N-terminus the amino acids
                                  (SEQ ID NO: 21)
WILVR.

(xix) WILV-KPC1 Δ 1-1253, lacks the amino
acids 1-1253 i.e
                                  (SEQ ID NO: 16)
WILVCPICYAHPISAVFQPCGHKSCKACINQHLMNNKDCFFCKTTIVSVE

DWEKGANTSTTSSAA.

It contains at its N-terminus the amino acids
                                  (SEQ ID NO: 22)
WILV.

(xx) WIL-KPC1 Δ 1-1253, i.e
                                  (SEQ ID NO: 17)
WILCPICYAHPISAVFQPCGHKSCKACINQHLMNNKDCFFCKTTIVSVED

WEKGANTSTTSSAA
lacks the amino acids 1-1253.

It contains at its N-terminus the amino acids
WIL.

Figure 3A:
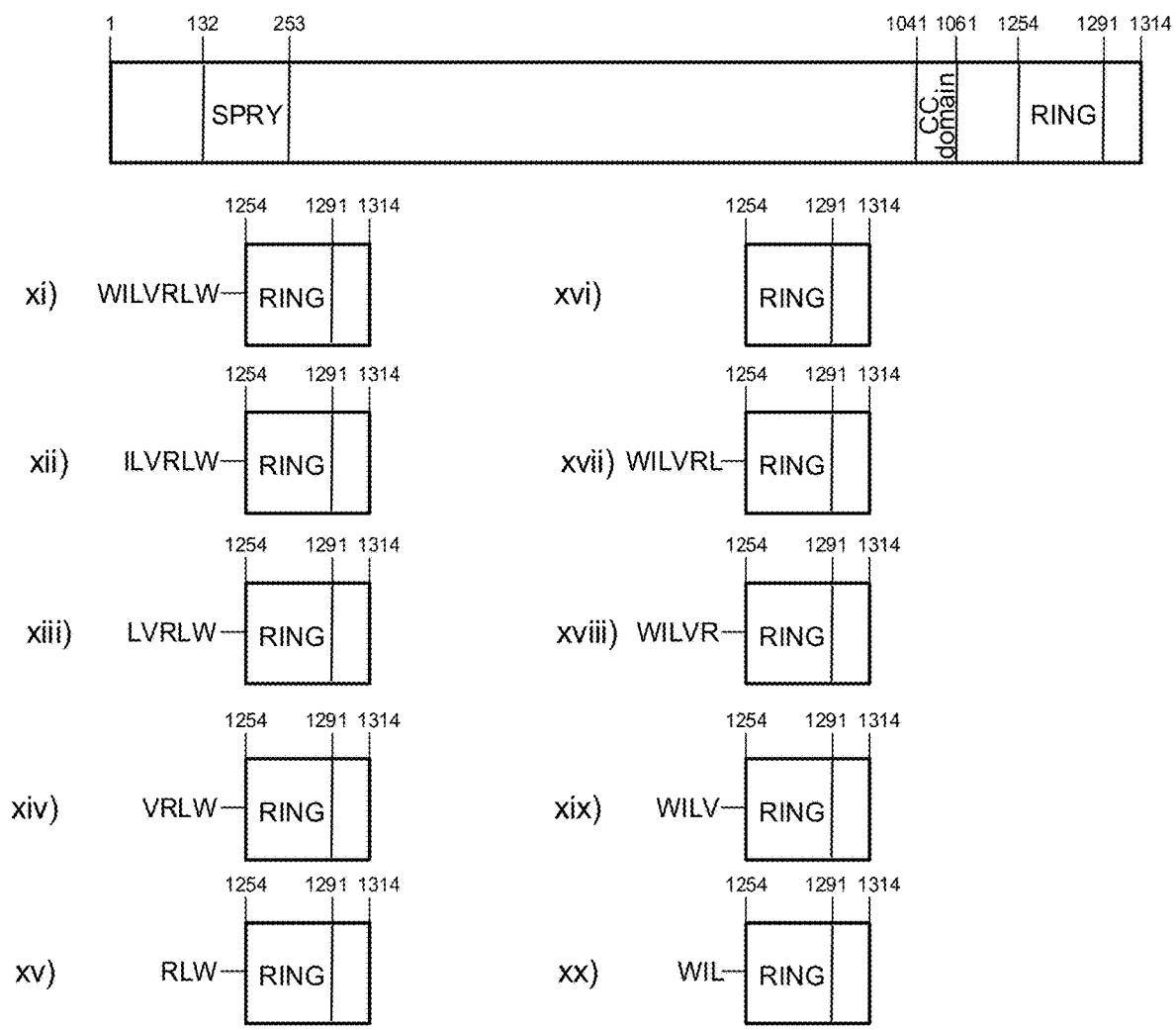
FIGS. 3A and 3B.
Figure 3B:
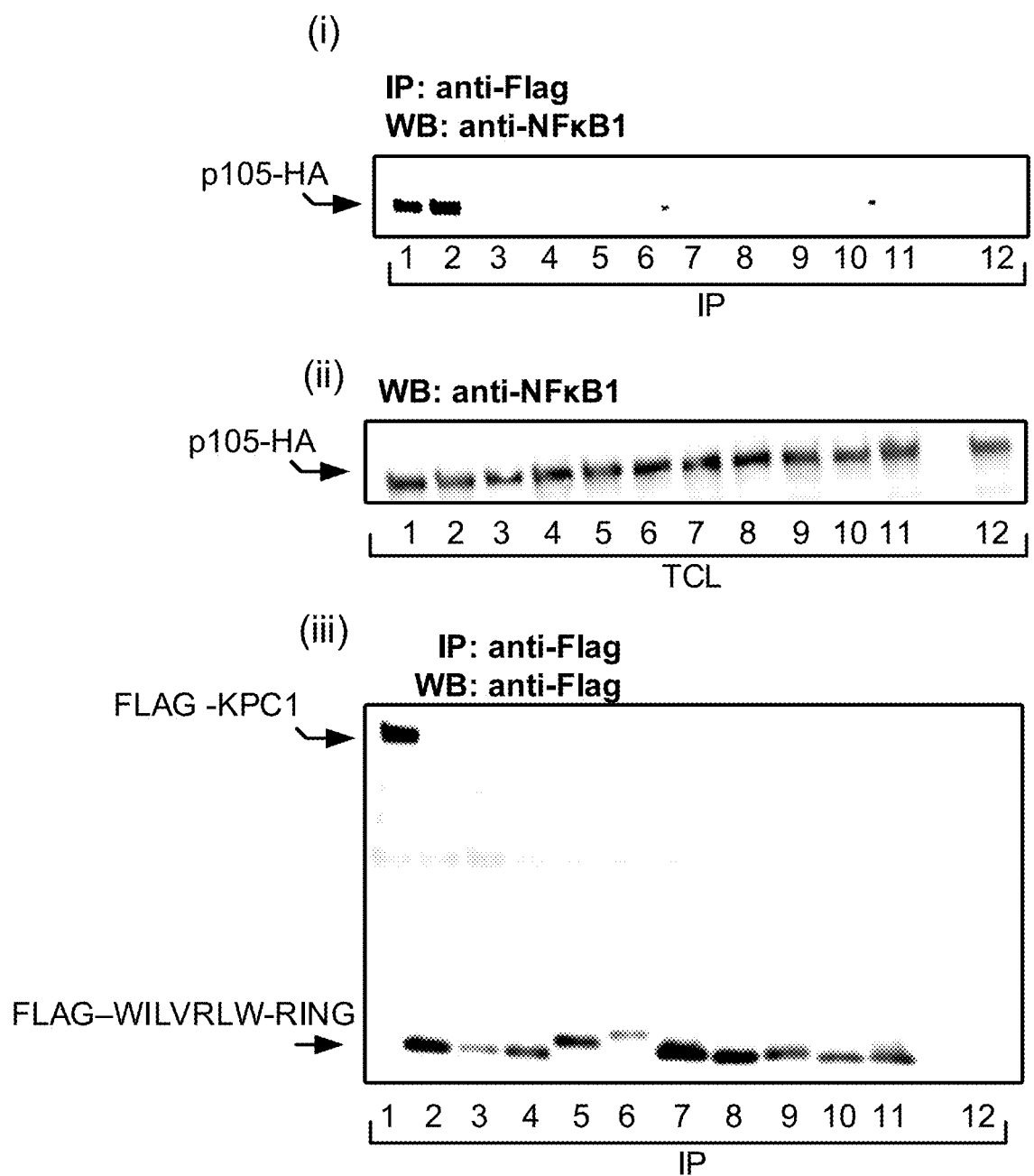

FIG. 3B is a western blot. HEK293T cells were transfected with cDNAs coding for p105-HA (lanes 1-12), along with different KPC1 species as following: KPC1-FLAG (lane 1), WILVRLW-KPC1 Δ 1-1253 (SEQ ID NO: 8) (lane 2), ILVRLW-KPC1 Δ 1-1253 (SEQ ID NO: 10) (lane 3), LVRLW-KPC1 Δ 1-1253 (SEQ ID NO: 11) (lane 4), VRLW-KPC1 Δ 1-1253 (lane 5) (SEQ ID NO: 12), RLW-KPC1 Δ 1-1253 (lane 6) SEQ ID NO:13), KPC1 Δ 1-1253 (lane 7), WILVRL-KPC1 Δ 1-1253 (lane 8) (SEQ ID NO: 14), WILVR-KPC1 Δ 1-1253 (SEQ ID NO: 15) (lane 9), WILV-KPC1 Δ 1-1253 (SEQ ID NO: 16) (lane 10), WIL-KPC1 Δ 1-1253 (SEQ ID NO: 17) (lane 11). Lane 12 represents cells that were transfected with empty vector. KPC1 species were immunoprecipitated using immobilized FLAG antibodies, resolved by SDS-page. NF-κB1 and KPC1 proteins were visualized by anti-NF-κB1 (FIG. 3B, (i, ii) and anti-FLAG (FIG. 3B, (iii) antibodies, respectively. 10% of the total cell lysate was analyzed for the expression of p105-HA (FIG. 3B, (ii)).

Figure 4A:
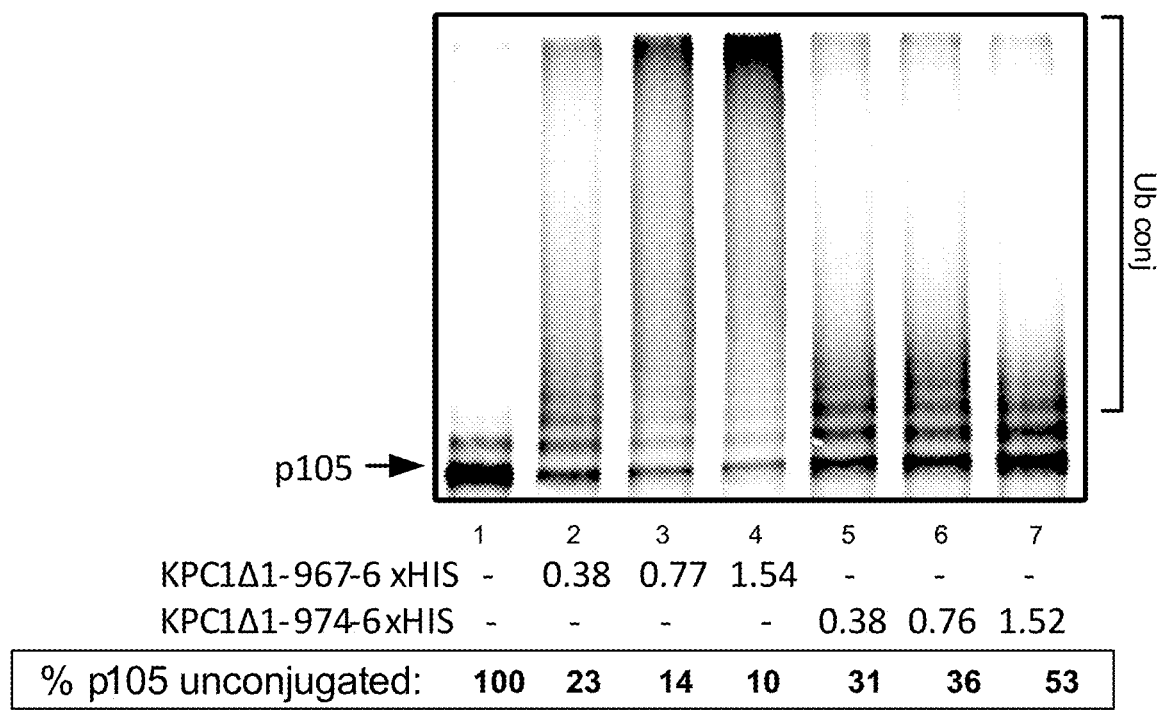
Figure 4B:
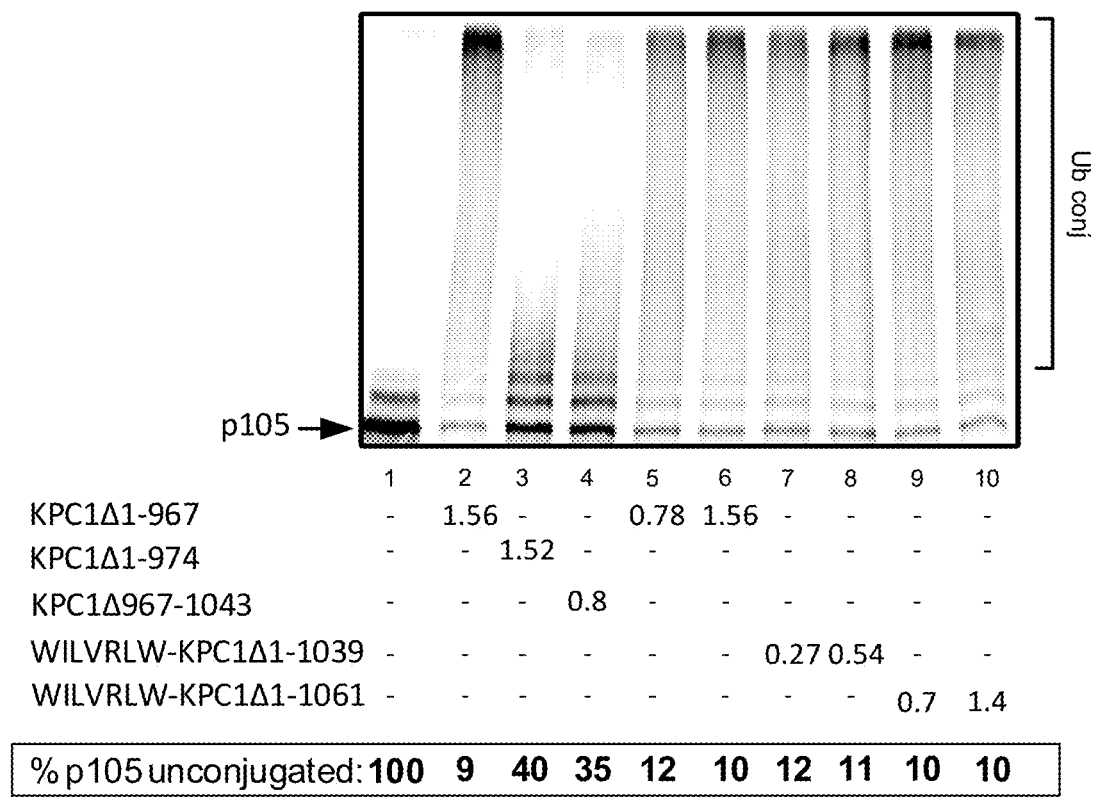

FIGS. 4A and 4B represent western blots showing in vitro ubiquitination of p105 by mutated species of KPC1: FIG. 4A: In vitro translated and $^{35}$S-labeled p105 was ubiquitinated by purified KPC1-Δ1-967-6xHIS (lanes 2-4) or KPC1-Δ1-974-6xHIS (lanes 5-7) in a reconstituted cell-free system. 4B) In vitro translated and $^{35}$S-labeled p105 was ubiquitinated by purified KPC1-Δ1-967-6xHIS (lanes 2,5, 6), KPC1-Δ1-974-6xHIS (lane 3), KPC1-Δ967-1043-6xHIS (lane 4), WILVRLW-KPC1-Δ1-1039-6xHIS (lanes 7-8) or WILVRLW-KPC1-Δ1-1061-6xHIS (lanes 9-10) in a reconstituted cell-free system.

Figure 5:
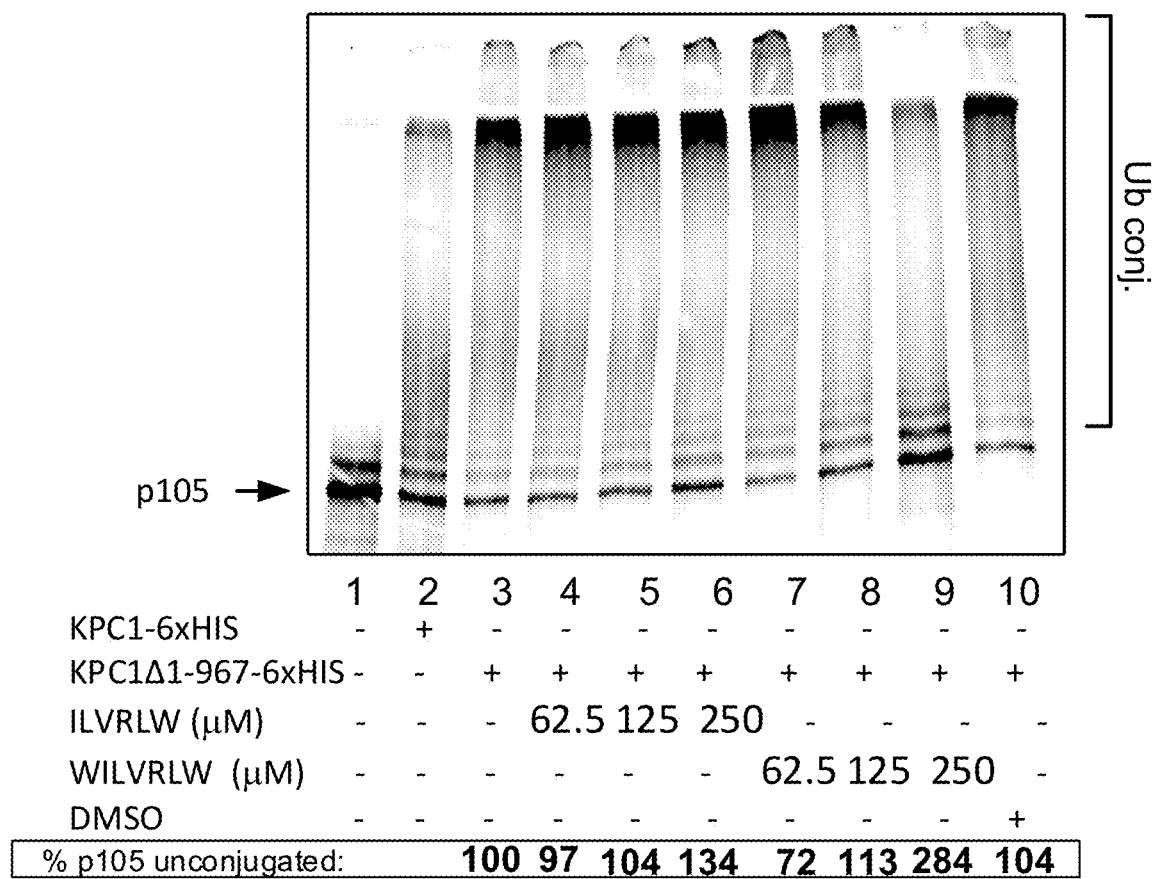

FIG. 5 demonstrates a western blot showing that a peptide of 7 amino acids, i.e. WILVRLW (SEQ ID NO: 1) inhibits ubiquitination of p105: in vitro translated and 35S-labeled p105 was ubiquitinated by purified KPC1-6xHIS (lane 2) or KPC1-Δ1-967-6xHIS (lanes 3-10) in a reconstituted cell-free system in the presence of the 7 amino acid peptide Amid-ILVRLW-Ac derived from the sequence of KPC1 that cannot bind p105 (lanes 4-6), or in the presence of Amid-WILVRLW-Ac peptide that interacts with p105 (lanes 7-9). Presented is the change (in %) of unconjugated p105 remained following addition of increasing concentrations of the peptides (compared to a system to which a peptide was not added; lane 3). Amid denotes N-terminal amidation and Ac denotes C-terminal acetylation.

Figure 6:
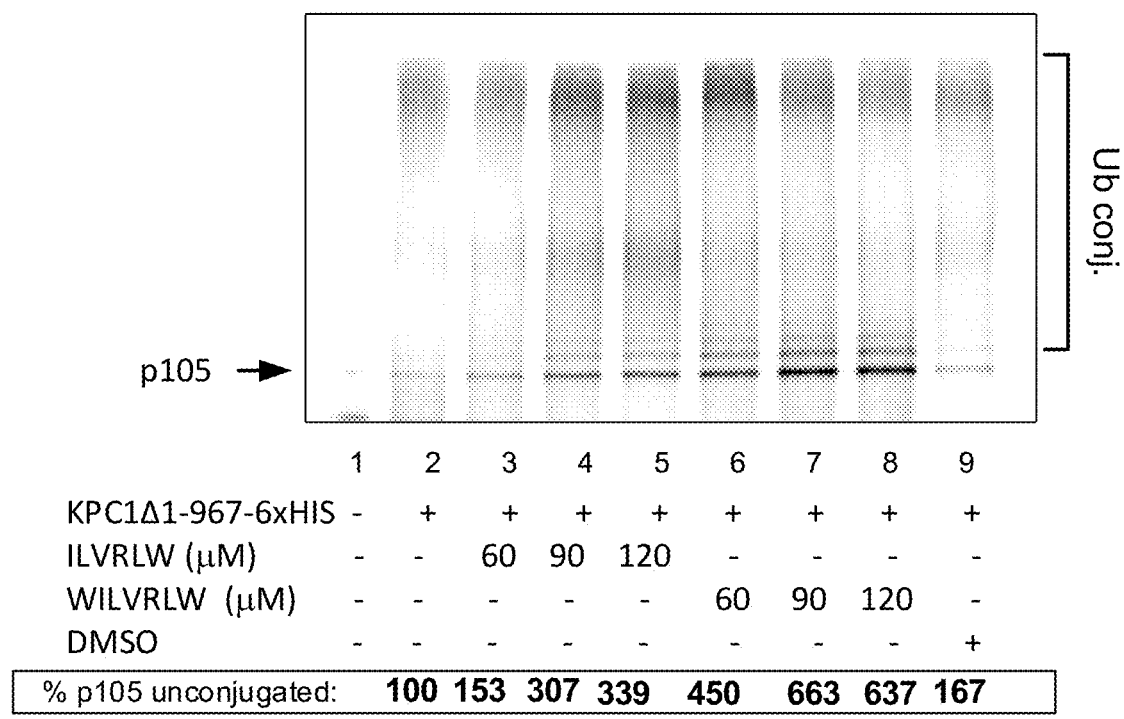

FIG. 6 demonstrates a western blot showing that a peptide of 7 amino acids WILVRLW corresponding to the sequence in KPC1 inhibits ubiquitination of p105: In vitro translated and $^{35}$S-labeled p105 was ubiquitinated by purified KPC1-Δ1-967-6xHIS (lanes 2-9) in a reconstituted cell-free system in the presence of the 6 amino acid peptide ILVRLW (SEQ ID NO: 9) derived from the sequence of KPC1 that cannot bind p105 (lanes 3-5), or in the presence of WILVRLW (SEQ ID. No. 1) peptide that interacts with p105 (lanes 6-8). Presented is the change (in %) of unconjugated p105 remained following addition of increasing concentrations of the peptides (compared to a system to which a peptide was not added; lane 2).

Figure 7:
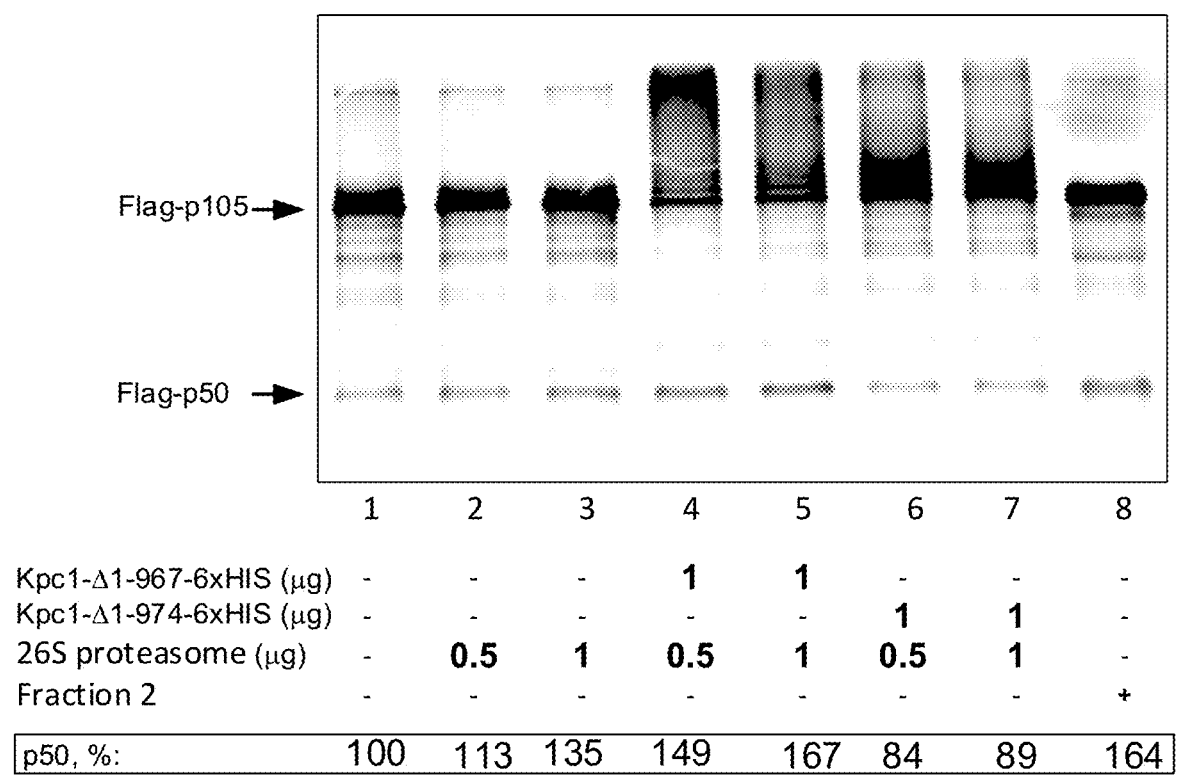

FIG. 7 demonstrates a northern blot showing that processing of p105 requires KPC1 that contains 7 amino acids sequence WILVRLW (SEQ ID. No. 1).

In vitro translated and $^{35}$S-labeled p105 was processed by purified proteasome (lanes 2-7) in the presence of purified KPC1-Δ1-967-6xHIS (lanes 4-5) or KPC1-Δ1-974-6xHIS (lanes 6-7) as indicated. Lane 8 represents processing of p105 in the system that contained Fraction 2. Cell extract is fractionated over the anion-exchange resin diethylaminoethyl (DEAE)-cellulose, where ubiquitin is eluted in Fraction I, the unabsorbed, flow-through material that contains also certain E2 enzymes. Fraction II, the high salt eluate, contains E1, the remaining E2s, all the E3s, and the 26S proteasome, but not free ubiquitin. Processing is the amount of p50 produced in the reaction. All values relate to 100%, which is the set point for processing of p105 in a system that lacks proteasome and KPC1 (lane 1).

Figure 8A:
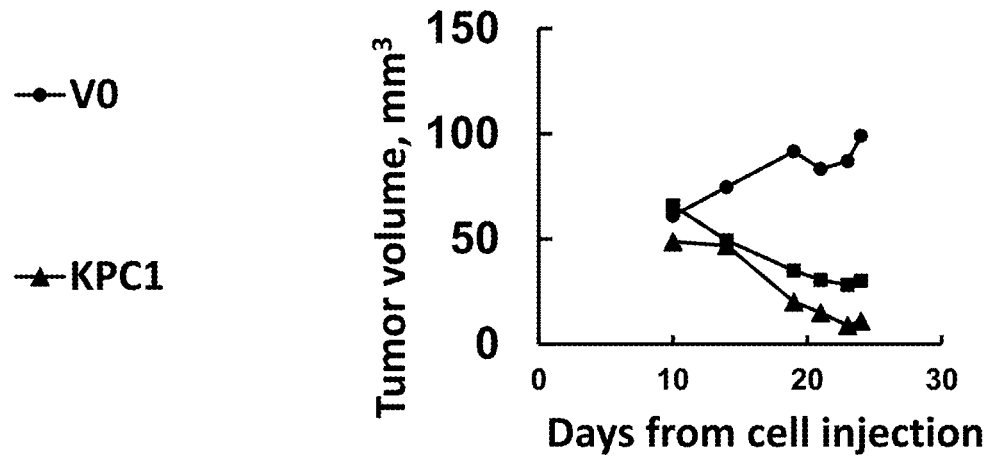
Figure 8B:
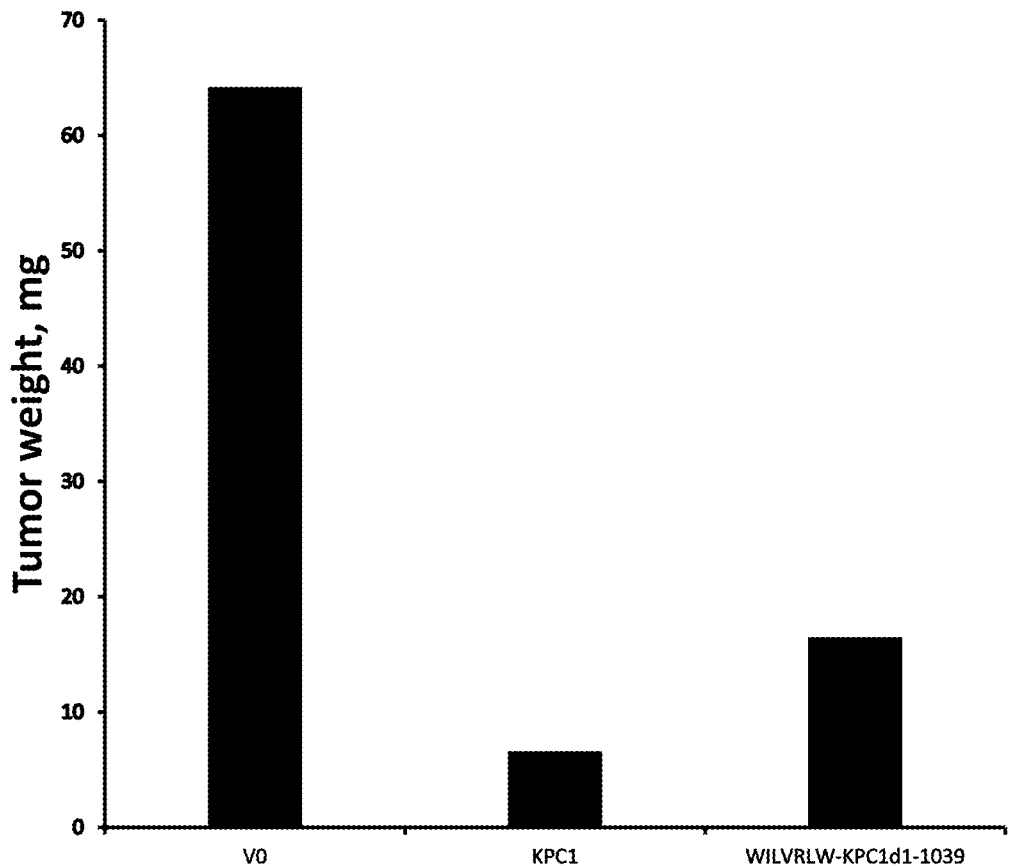
Figure 8C:
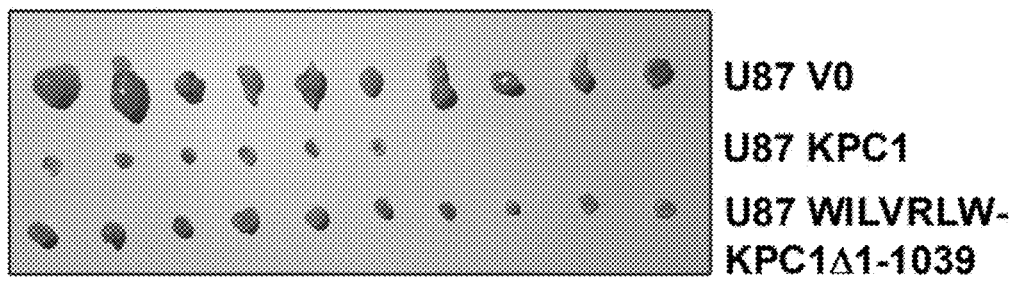

FIGS. 8A, B and C demonstrates experiment that was carried out in vivo in nude mice. Overexpression of WIL-VRLW-KPC1Δ1-1039 (SEQ ID NO: 6) in U87-MG cells injected to the mice repressed glioblastoma U87-MG tumor growth in the similar manner as overexpression of KPC1 in the U87-MG cells indicating that the truncated species mimics the function of the wild type protein almost completely. FIG. 8A and FIG. 8B depict growth rates and weights of tumor xenografts grown in nude mice, and derived from U87-MG expressing V0 (control), Myc-KPC1 or Flag-WILVRLW-KPC1Δ1-1039 (SEQ ID NO: 6). FIG. 8C shows photographs of tumors derived from U87MG cells that stably express Myc-KPC1 or Flag-WILVRLW-KPC1Δ1-1039 (SEQ ID NO: 6) used in the experiment three weeks after inoculation.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In the current invention, the inventors identified, in cellulo, that KPC1 interacts with p105 through seven amino acids, WILVRLW, which comprise positions 968-974 in the sequence of the KPC1 protein.

Embodiments of the invention are directed to a peptide comprising the amino acid sequence set forth in WILVRLW (SEQ ID NO: 1), or any functionally related variant thereof. In some embodiments, the peptide includes between 7-20 amino acids. In some embodiments, the peptide includes between 7-15 amino acids. In some embodiments, the peptide includes between 7-10 amino acids. Such a peptide interacts with p105.

Further embodiments of the invention are directed to complex comprising a peptide comprising the amino acid sequence set forth in WILVRLW (SEQ ID NO: 1), or any functionally related variant thereof. Further embodiments of the invention are directed to a peptide having at least 75, 76, 77, 78, 79, 80, 81, 82, 83, 84, 85, 86, 87, 88, 89, 90, 91, 92, 93, 94, 95, 96, 97, 98, 99% homology to the peptide comprising the amino acid sequence set forth in WILVRLW (SEQ ID NO: 1), as disclosed herein. Such a peptide interacts with p105.

Further embodiments of the invention are directed to a complex comprising a peptide comprising the amino acid sequence set forth in WILVRLW (SEQ ID NO: 1, or any functionally related variant thereof, or to a peptide having at least 75, 76, 77, 78, 79, 80, 81, 82, 83, 84, 85, 86, 87, 88, 89, 90, 91, 92, 93, 94, 95, 96, 97, 98, 99% homology to the amino acid sequence set forth in WILVRLW (SEQ ID NO: 1), wherein the peptide is bound to a linker and wherein the linker is bound to RING. Examples of such a complex is without being limited WILVRLW-KPC1Δ1-1039 i.e.
(SEQ ID NO: 6)
WILVRLWAFSEFIGMIQEIQQAAERLERNFVDSRQLKVCATCFDLSVSLL

RVLEMTITLVPEIFLDWTRPTSEMLLRRLAQLLNQVLNRVTAERNLFDRV

VTLRLPGLESVDHYPILVAVTGILVQLLVRGPASEREQATSVLLADPCFQ

LRSICYLLGQPEPPAPGTALPAPDRKRFSLQSYADYISADELAQVEQMLA

HLTSASAQAAAASLPTSEEDLCPICYAHPISAVFQPCGHKSCKACINQHL

MNNKDCFFCKTTIVSVEDWEKGANTSTTSSAA

WILVRLW-KPC1Δ1-1061 i.e
(SEQ ID NO: 7)
WILVRLWFVDSRQLKVCATCFDLSVSLLRVLEMTITLVPEIFLDWTRPTS

EMLLRRLAQLLNQVLNRVTAERNLFDRVVTLRLPGLESVDHYPILVAVTG

ILVQLLVRGPASEREQATSVLLADPCFQLRSICYLLGQPEPPAPGTALPA

PDRKRFSLQSYADYISADELAQVEQMLAHLTSASAQAAAASLPTSEEDLC

PICYAHPISAVFQPCGHKSCKACINQHLMNNKDCFFCKTTIVSVEDWEKG

ANTSTTSSAA
and

WILVRLW-KPC1Δ1-967 i.e.
(SEQ ID NO: 5)
WILVRLWRGCGFGYRYTRLPHLLKTKLEDANLPSLQKPCPSTLLQQHMAD

LLQQGPDVAPSFLNSVLNQLNWAFSEFIGMIQEIQQAAERLERNFVDSRQ

LKVCATCFDLSVSLLRVLEMTITLVPEIFLDWTRPTSEMLLRRLAQLLNQ

VLNRVTAERNLFDRVVTLRLPGLESVDHYPILVAVTGILVQLLVRGPASE

REQATSVLLADPCFQLRSICYLLGQPEPPAPGTALPAPDRKRFSLQSYAD

YISADELAQVEQMLAHLTSASAQAAAASLPTSEEDLCPICYAHPISAVFQ

PCGHKSCKACINQHLMNNKDCFFCKTTIVSVEDWEKGANTSTTSSAA.

In some embodiments of the invention, the RING (Really Interesting New Gene) is a RING domain, which is a special type of zinc binding domain. The consensus RING sequence is $CX_2CX_{(9-39)}CX_{(1-3)}HX_{(2-3)}C/HX_2CX_{(4-48)}CX_2C$ with eight cysteines and histidines in a "cross-brace" topology to coordinate two zinc ions.

In some embodiments the RING contains the amino acid sequence of CPICYAHPISAVFQPCGHKSCK-ACINQHLMNNKDCFFC (SEQ ID. No. 4).

The RING may in some embodiments contain from between 40 to 60 amino acids.

In some embodiments the RING contains from between 30 to 70 amino acids. In some embodiments the RING contains from between 45 to 55 amino acids. In some embodiments the RING contains from between 35 to 65 amino acids. In some embodiments the RING contains from between 47 to 52 amino acids.

In some embodiments of the invention the linker may comprise between 2-300 amino acids. In some embodiments of the invention the linker may comprise between 2-30 amino acids. In some embodiments of the invention the linker may comprise between 200-300 amino acids. In some embodiments of the invention the linker may comprise between 100-199 amino acids. In some embodiments of the invention the linker may comprise between 10-99 amino acids. In some embodiments of the invention the linker may comprise between 2-20 amino acids. In some embodiments of the invention the linker may comprise between 2-15 amino acids. In some embodiments of the invention the linker may comprise between 2-10 amino acids.

In some embodiments of the invention the linker may comprise between 2-8 amino acids.

According to some embodiments of the invention, there is provided a chimera or a conjugate comprising the amino acid sequence set forth in WILVRLW (SEQ ID NO: 1), or any functionally related variant thereof, or a peptide having at least 75, 76, 77, 78, 79, 80, 81, 82, 83, 84, 85, 86, 87, 88, 89, 90, 91, 92, 93, 94, 95, 96, 97, 98, 99% homology to the amino acid sequence set forth in WILVRLW (SEQ ID NO: 1), conjugated with or without a linker to a small molecule that recruits E3 ligase as described herein. Example to such a chimera or conjugate is without any limitation is:

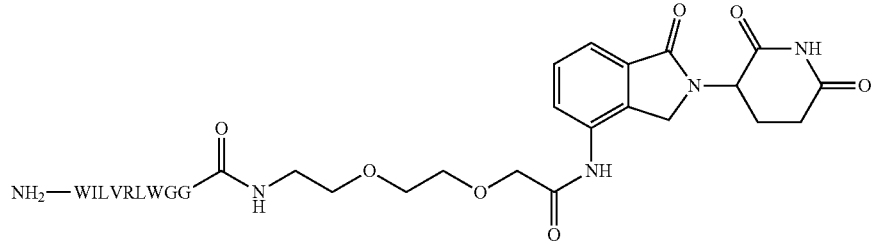

Such an exemplary chimera contains the peptide of SEQ ID NO: 1 linked to a GG that is connected to a small molecule derived from lenalidomide.

Further embodiments of the invention are directed to a functionally equivalent molecule that mimics a functional activity of the peptide disclosed herein in SEQ ID. No. 1, and of any of the functionally related variants thereof, wherein the molecule is a peptidomimetic or a stapled peptide or a chemical compound. This functionally equivalent molecule may replace the WILVRLW (SEQ ID NO: 1) in the above identified complex which further comprises a linker and RING.

In some embodiments of the invention the functionally equivalent molecule that mimics a functional activity of the peptide disclosed herein is SEQ ID. No. 1, and of any of the functionally related variants thereof, wherein the molecule is a peptidomimetic or a stapled peptide or a chemical compound is conjugated with or without a linker to a small molecule that recruits E3 ligase, thereby forming a conjugate. Such a small molecule that recruits ubiquitin ligase (E3) may be for example, without limitation Lenalidomid or Thalidomid.

A proteolysis targeting chimera (PROTAC) is a heterofunctional small molecule composed of two active domains and a linker capable of removing specific unwanted proteins. Rather than acting as a conventional enzyme inhibitor, a PROTAC works by inducing selective intracellular proteolysis. PROTACs consist of two covalently linked protein-binding molecules: one capable of engaging an E3 ubiquitin ligase, and another that binds to a target protein meant for degradation. Recruitment of the E3 ligase to the target protein results in ubiquitination and subsequent degradation of the target protein by the proteasome In some embodiments, the linker in PROTAC molecule may be hexa-glycine, i.e GGGGGG according to SEQ ID NO: 3.

Additional embodiments are directed to a pharmaceutical composition comprising a therapeutically effective amount of a peptide disclosed herein or comprising a functionally equivalent molecule, as disclosed, and a pharmaceutically acceptable carrier or excipient.

Additional embodiments are directed to a pharmaceutical composition comprising a therapeutically effective amount of a complex comprising the peptide disclosed herein, or comprising a functionally equivalent molecule, as disclosed, and a pharmaceutically acceptable carrier or excipient, wherein the peptide or the functionally equivalent molecule is linked to a linker that is bound to RING.

Additional embodiments are directed to a pharmaceutical composition comprising a therapeutically effective amount of conjugate comprising a functionally equivalent molecule, as disclosed herein, and a pharmaceutically acceptable carrier or excipient, wherein the functionally equivalent molecule is linked with or without a linker to a small molecule that recruits E3 ligase.

Additional embodiments are directed to a vaccine comprising an effective amount of a peptide or a functionally equivalent molecule disclosed herein and optionally an adjuvant.

Additional embodiments are directed to a vaccine comprising an effective amount of the complex or the conjugate that comprises a functionally equivalent molecule as disclosed herein and optionally an adjuvant.

In an embodiment of the invention, the functionally related peptide variant of this invention comprises substitution, deletion, and/or insertion at one or more positions in the peptide set forth in SEQ ID NO: 1.

In an embodiment of the invention, the functionally related peptide variant of this invention comprises conservatively modified variants substitution at one or more positions in the peptide set forth in SEQ ID NO: 1.

In some embodiments of the invention, the peptide may have at least 70%, 75%, 80%, 85%, 90%, 95% or 99% sequence identity to the amino acid sequence set forth in WILVRLW (SEQ ID NO: 1).

In some embodiments of the invention, the amino acids of the peptide are of L or D stereoisomers or combination thereof.

In one embodiment of the invention, this invention provides a functionally equivalent molecule that mimics the functional activity of any of the peptide or peptide variants provided in this invention. The term "functionally equivalent molecule" refers in the application to any compound such as but not restricted to peptidomimetic or stapled peptide. The functionally equivalent molecule may be obtained by retro-inverso or D-retro-enantiomer peptide technique, consisting of D-amino acids in the reversed sequence. The functionally equivalent molecule may be obtained by using amino acid derivative.

As used herein, in one embodiment, the term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NH-G(Sc)—C(0)-Q or —OC(0)G($S_c$)-Q, wherein Q is —SR, —NRR or alkoxyl, R is hydrogen or alkyl, $S_c$ is a side chain of a naturally occurring or non-naturally occurring amino acid and G is $C_1$-$C_2$ alkyl. In certain embodiments, G is Ci alkyl and Sc is selected from the group consisting of hydrogen, alkyl, heteroalkyl, arylalkyl and heteroarylalkyl.

As used herein, in one embodiment, the term "peptide" may be derived from a natural biological source, synthesized, or produced by recombinant technology. It may be generated in any manner, including by chemical synthesis. One or more of the amino acids may be modified, for example, by the addition of a chemical entity such as a carbohydrate group, a phosphate group, a farnesyl group, an isofamesyt group, a fatty acid group, an acyl group (e.g., acetyl group), a linker for conjugation, functionalization, or other known protecting/blocking groups.

As used herein, in one embodiment, the term "peptide," may be fragments, derivatives, analogs, or variants of the foregoing peptides, and any combination thereof. Fragments of peptides, as that term or phrase is used herein, include proteolytic fragments, as well as deletion fragments. Variants of peptides include fragments and peptides with altered amino acid sequences due to amino acid substitutions, deletions, or insertions.

Variants may occur naturally or be non-naturally occurring. Examples include fusion proteins, peptides having one or more residues chemically derivatized by reaction of a functional side group, and peptides that contain one or more naturally occurring amino acid derivatives of the twenty standard amino acids. These modifications may also include the incorporation of D-amino acids, or other non-encoded amino-acids. In one embodiment, none of the modifications should substantially interfere with the desired biological activity of the peptide, fragment thereof. In another embodiment, modifications may alter a characteristic of the peptide, fragment thereof, for instance stability or half-life, without interfering with the desired biological activity of the peptide, fragment thereof. In one embodiment, as used herein the terms "peptide" and "protein" may be used interchangeably having all the same meanings and qualities.

In one embodiment, peptides according to the invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the peptide of the present invention and fused cleavable moiety. In one embodiment, a fusion protein can be designed so that the peptide can be readily isolated by affinity chromatography; e.g., by immobilization on a column specific for the cleavable moiety. In one embodiment, a cleavage site is engineered between the peptide and the cleavable moiety and the peptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the peptide of the present invention is retrieved in a substantially pure form.

In one embodiment, the phrase "substantially pure" refers to a purity that allows for the effective use of the protein in the applications described herein.

In one embodiment, the peptide of the present invention can also be synthesized using in vitro expression systems. In one embodiment, in vitro synthesis methods are well known in the art and the components of the system are commercially available.

In one embodiment, production of a peptide of this invention is using recombinant DNA technology. A "recombinant" peptide, or protein refers to a peptide, or protein produced by recombinant DNA techniques; i.e., produced from cells transformed by an exogenous DNA construct encoding the desired peptide or protein.

In some embodiments, the recombinant peptides, fragments thereof or peptides are synthesized and purified; their therapeutic efficacy can be assayed either in vivo or in vitro. In one embodiment, the activities of the recombinant fragments or peptides of the present invention can be ascertained using various assays including cell viability, survival of transgenic mice, and expression of megakaryocytic and lymphoid RNA markers.

In one embodiment, a peptide of this invention comprises at least 3 amino acids. In another embodiment, a peptide comprises at least 5 amino acids. In another embodiment, a peptide comprises at least 7 amino acids. In one embodiment, a peptide of this invention consists essentially of at least 5 amino acids. In another embodiment, a peptide consists essentially of 7 amino acids.

In some embodiments of the invention, the linker may comprise at least 2, 3, or 4 amino acids. In some embodiments of the invention, the linker may comprise at least 5 amino acids. In another embodiment, the linker comprises at least 7 amino acids. In some embodiments, the linker may comprise at least 20 amino acids. In another embodiment, the linker comprises at least 25 amino acids. In other embodiments, the linker comprises at least 30 amino acids or at least 50 amino acids or 75 amino acids, or 100 amino acids, or 125 amino acids, or 150 amino acids, or 200 amino acids, or 250 amino acids or 300 amino acids.

As used herein, in one embodiment, the terms "peptide" and "fragment" may be used interchangeably having all the same meanings and qualities. As used herein in, in one embodiment the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein under.

Peptide bonds (—CO—NH—) within the peptide may be substituted, for example, by N-methylated bonds (—N(CH3)—CO—), ester bonds (—C(R)H—C—O—O—C(R)—N—), ketomethylen bonds (—CO—CH2—), α-aza bonds (—NH—N(R)—CO—), wherein R is any alkyl, e.g., methyl, carba bonds (—CH2—NH—), hydroxyethylene bonds (—CH(OH)—CH2—), thioamide bonds (—CS—NH—), olefinic double bonds (—CH=CH—), retro amide bonds (—NH—CO—), peptide derivatives (—N(R)—

CH2—CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In one embodiment, the peptide of this invention further comprises a detectable tag. As used herein, in one embodiment the term "detectable tag" refers to any moiety that can be detected by a skilled practitioner using art known techniques. Detectable tags for use in the screening methods of the present invention may be peptide sequences. Optionally the detectable tag may be removable by chemical agents or by enzymatic means, such as proteolysis. For example the term "detectable tag" includes chitin binding protein (CBP)-tag, maltose binding protein (MBP)-tag, glutathione-S-transferase (GST)-tag, poly(His)-tag, FLAG tag, Epitope tags, such as, V5-tag, c-myc-tag, and HA-tag, and fluorescence tags such as green fluorescent protein (GFP), red fluorescent protein (RFP), yellow fluorescent protein (YFP), blue fluorescent protein (BFP), and cyan fluorescent protein (CFP); as well as derivatives of these tags, or any tag known in the art. The term "detectable tag" also includes the term "detectable marker".

In one embodiment, a peptide of this invention is an isolated peptide. Such an isolated peptide may include a peptide-tag.

As used herein, in one embodiment the term "amino acid" refers to naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. As used herein, in one embodiment the phrase "Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified variations. Every nucleic acid sequence herein which encodes a polypeptide also describes silent variations of the nucleic acid. One of skill in the art will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant", including where the alteration results in the substitution of an amino acid with a chemically similar amino acid. Conservative substitution tables providing functionally similar amino acids are well known in the art. Guidance concerning which amino acid changes are likely to be phenotypically silent can also be found in Bowie et al., 1990, Science 247: 1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

Polynucleotide

Embodiments of the invention are directed to an isolated polynucleotide encoding a peptide as set forth in WILVRLW (SEQ ID NO: 1), or any functionally related variant, thereof or a complex comprising the peptide, or any functionally related variant thereof, as disclosed herein.

Further embodiments of the invention are directed to a plasmid or a vector comprising the isolated polynucleotide, as disclosed herein. Additional embodiments are directed to a pharmaceutical composition comprising a therapeutically effective amount of the polynucleotide disclosed herein and a pharmaceutically acceptable carrier or excipient.

In some embodiments of the invention, there is provided a polynucleotide encoding the complex of the invention which comprises a peptide comprising the amino acid sequence set forth in WILVRLW (SEQ ID NO: 1), or any of the functionally related peptide variants thereof as provided herein, wherein the peptide is linked to a linker that is linked to RING. In some embodiments this invention, there is provided a plasmid or a vector comprising a polynucleotide which encodes the complex that includes a peptide having the amino acid sequence set forth in WILVRLW (SEQ ID NO: 1), or any of the functionally related peptide variants thereof as provided herein, which are linked to a linker that is linked to RING.

In some embodiments of the invention, there is provided a polynucleotide encoding the conjugate of the invention which comprises a peptide comprising the amino acid sequence set forth in WILVRLW (SEQ ID NO: 1), or any of the functionally related peptide variants thereof as provided herein, wherein the peptide is linked to a linker that is linked to a peptide that recruits E3 ligase. In some embodiments this invention, there is provided a plasmid or a vector comprising a polynucleotide which encodes the complex that includes a peptide having the amino acid sequence set forth in WILVRLW (SEQ ID NO: 1), or any of the functionally related peptide variants thereof as provided herein, which are linked to a linker that is linked to peptide that can recruit E3 ligase.

In one embodiment, the nucleic acid molecules, of this invention may be an isolated nucleic acid molecule.

As used herein, in one embodiment the term "isolated" means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for example for mutagenesis, to form fusion proteins, to form expression vectors, to form tagged proteins or peptides, for in vitro expression, and for propagation or expression in a host. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides, polypeptides and peptides may occur in a composition, such as a media, formulations, solutions for introduction of polynucleotides, polypeptides or peptides, for example, into cells, compositions or solutions for chemical or enzymatic reactions, for instance, which are not naturally occurring compositions, and, therein remain isolated polynucleotides or polypeptides within the meaning of that term as it is employed herein.

As used herein, in one embodiment the term "nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof.

A nucleic acid "backbone" may be made up of a variety of linkages, including one or more of sugar-phosphodiester linkages, peptide-nucleic acid bonds), phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., The Biochemistry of the Nucleic Acids 5-36, Adams et ah, ed., 1 1th ed., 1992; Abraham et al, 2007, BioTechniques 43: 617-24), which include derivatives of purine or pyrimidine bases (e.g., N4-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, 06-methylguanine, 4-thio-pyrimidines, 4-amino-pyrimidines, 4-dimethylhydrazine-pyrimidines, and 04-alkyl-pyrimidines, and pyrazolo-compounds, such as unsubstituted or 3-substituted pyrazolo[3,4-d]pyrimidine). Nucleic acids may include "abasic" residues in which the backbone does not include a nitrogenous base for one or more residues.

A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et ah, Biochemistry 43: 13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid. As used herein, in one embodiment the terms "nucleic acid molecule", "polynucleotide" and "nucleotide" may be used interchangeably having all the same meanings and qualities.

As used herein, in one embodiment the term "nucleotide" is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-0-Me). As used herein, methoxy oligonucleotides containing "T" residues have a methoxy group at the 2' position of the ribose moiety, and a uracil at the base position of the nucleotide.

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

In one embodiment, the term "nucleic acid" or "oligonucleotide" refers to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The nucleic acids can be produced by any synthetic or recombinant process, which are well known in the art.

Nucleic acids can further be modified to alter biophysical or biological properties by means of techniques known in the art. For example, the nucleic acid can be modified to increase its stability against nucleases (e.g., "end-capping"), or to modify its solubility, or binding affinity to complementary sequences. These nucleic acids may comprise the vector, the expression cassette, the promoter sequence, the gene of interest, or any combination thereof. In another embodiment, its lipophilicity may be modified, which, in turn, will reflect changes in the systems employed for its delivery, and in one embodiment, may further be influenced by whether such sequences are desired for retention within, or permeation through the skin, or any of its layers. Such considerations may influence any compound used in this invention, in the methods and systems described.

In one embodiment, DNA can be synthesized chemically from the four nucleotides in whole or in part by methods known in the art. Such methods include those described in Caruthers (1985; Science 230:281-285). DNA can also be synthesized by preparing overlapping double-stranded oligonucleotides, filling in the gaps, and ligating the ends together (see, generally, Sambrook et al. (1989; Molecular Cloning—A Laboratory Manual, 2nd Edition. Cold Spring Habour Laboratory Press, New York)). In another embodiment, mutations may be prepared from wild-type DNA by site-directed mutagenesis (see, for example, Zoller et al. (1982; DNA. 1984 Dec;3(6):479-88); Zoller (1983); and Zoller (1984; DNA. 1984 Dec;3(6):479-88); McPherson (1991; Directed Mutagenesis: A Practical Approach. Oxford University Press, NY)). The DNA obtained can be amplified by methods known in the art. One suitable method is the polymerase chain reaction (PCR) method described in Saiki et al. (1988; Science. 1988 Jan. 29; 239(4839):487-491), Mullis et al., U.S. Pat. No. 4,683,195, and Sambrook et al. (1989).

Methods for modifying nucleic acids to achieve specific purposes are disclosed in the art, for example, in Sambrook et al. (1989). Moreover, the nucleic acid sequences of the invention can include one or more portions of nucleotide sequence that are non-coding for the protein of interest. Variations in DNA sequences, which are caused by point mutations or by induced modifications (including insertion, deletion, and substitution) to enhance the activity, half-life or production of the polypeptides encoded thereby, are also encompassed in the invention.

As will be appreciated by one skilled in the art, a fragment or derivative of a nucleic acid sequence or gene that encodes for a protein or peptide can still function in the same manner as the entire wild type gene or sequence. Likewise, forms of nucleic acid sequences can have variations as compared to wild type sequences, nevertheless encoding the protein or peptide of interest, or fragments thereof, retaining wild type function exhibiting the same biological effect, despite these variations. Each of these represents a separate embodiment of this present invention.

In some embodiments, this invention provides an isolated polynucleotide encoding the peptide or the peptide variants of this invention. In some embodiments, this invention provides a plasmid or any other vector comprising an isolated polynucleotide encoding the peptide or peptide variants of this invention.

In some embodiments, this invention provides an isolated polynucleotide encoding the antibody or the antibody binding fragment of this invention. In some embodiments, this invention provides a plasmid or any other vector comprising an isolated polynucleotide encoding the antibody or the antibody binding fragment of this invention.

In one embodiment, the term "vector" or "expression vector" refers to a carrier molecule into which a nucleic acid sequence can be inserted for introduction into a cell where it can be replicated. In one embodiment, the nucleic acid molecules are transcribed into RNA, which in some cases are then translated into a protein, polypeptide, or peptide. In one embodiment, expression vectors can contain a variety of "control sequences" which refer to nucleic acid sequences necessary for the transcription and possibly translation of an operably linked coding sequence in a particular host cell. In another embodiment, a vector further includes an origin of replication. As used herein, the term "control sequence" may also be referred to herein as a "regulatory sequence". In one embodiment the vector may be a shuttle vector, which in one embodiment can propagate both in prokaryotic and eukaryotic cells, or in another embodiment, the vector may be constructed to facilitate its integration within the genome of an organism of choice.

As used herein, the terms "vector" and "expression vector" may be used interchangeably having all the same meanings and qualities. In one embodiment, as used herein the term "expression vector" refers to a DNA construct comprising an essential control component which is operably linked to an insert gene so that the insert gene is only expressed when introduced into the host cell. In another embodiment, the term "expression vector" refers to a DNA construct comprising an essential control component which is operably linked to an insert gene so that the insert gene is may be expressed in an in vitro expression system as is known in the art. The expression vector may be prepared and purified by a standard recombinant DNA technology. The type of the expression vector is not particularly limited, as long as it may express and produce a target gene, in vitro and/or in a variety of host cells of prokaryotic and eukaryotic cells. In one embodiment, the expression vector is a vector capable of producing a large amount of a recombinant protein, which may be a protein or peptide or antibody or antibody binding fragment of this invention, in a similar form to the native protein or peptide or antibody or antibody binding fragment while it retains a strong promoter activity and a strong expression ability. The expression vector is preferably a vector comprising at least a promoter, a start codon, a gene encoding a target protein, a stop codon, and a terminator. In addition, it may comprise a DNA encoding a signal peptide, an enhancer sequence, untranslated regions at the 5' and 3' ends of a target gene, a selectable marker region or a replicable unit, etc., if desired. Moreover, the type of the expression vector may be a mono-cistronic vector including a polynucleotide encoding one recombinant protein, a bi-cistronic vector including a polynucleotide encoding two recombinant proteins, a poly-cistronic vector including a polynucleotide encoding three recombinant proteins or more. In one embodiment, a promoter is a Vav promoter.

The vector, in other embodiments may be, for example, a plasmid, a bacmid, a phagemid, a cosmid, a phage, a virus or an artificial chromosome. In one embodiment, the vector is a viral vector, which in one embodiment may be a bacteriophage, mammalian virus, or plant virus.

In one embodiment, the viral vector is an adenoviral vector. In another embodiment, the adenovirus may be of any known serotype or subgroup. In another embodiment, the viral vector is an adeno associated viral vector. In another embodiment, the adenoviral vector is a helper-dependent adenoviral vector ("HDAD", "HD" or "HDAd" or "HD-Ad"), which in another embodiment, is synonymous with gutless, gutted, mini, fully deleted, high-capacity, Δ, or pseudo adenovirus, and which in another embodiment are deleted of all viral coding sequences except for sequences supporting DNA replication, which in one embodiment, comprise the adenovirus inverted terminal repeats and packaging sequence (ψ). In another embodiment, helper-dependent adenoviruses express no viral proteins.

In another embodiment, the viral vector is an adeno associated viral vector. In another embodiment, the viral vector is a retroviral vector.

In other embodiments, the viral vector is derived from a virus such as vaccinia virus, lentivirus, polio virus, hepatitis virus, papilloma virus, cytomegalovirus, simian virus, or herpes simplex virus.

In certain embodiments of the invention, the vector comprising a nucleic acid sequence may comprise naked recombinant DNA or plasmids. Transfer of the construct may be performed by any method which physically or chemically permeabilizes the cell membrane. In one embodiment, the vector is a mini-circle DNA, which in one embodiment, is a supercoiled DNA molecule for non-viral gene transfer, which has neither a bacterial origin of replication nor an antibiotic resistance marker. In another embodiment, mini-circle DNA comprises no bacterial control regions from gene delivery vectors during the process of plasmid production. They are thus smaller and potentially safer than other plasmids used in gene therapy. In one embodiment, mini-circle DNA produce high yield, are simple to purify, and provide robust and persistent transgene expression.

Construction of vectors using standard recombinant techniques is well known in the art (see, for example, Maniatis, et al., Molecular Cloning, A Laboratory Manual (Cold Spring Harbor, 1990) and Ausubel, et al., 1994, Current Protocols in Molecular Biology (John Wiley & Sons, 1996), both incorporated herein by reference).

In one embodiment, a vector comprising a nucleic acid encoding a therapeutic peptide or antibody or antibody biding fragment of the instant invention is introduced into a host cell. There are a number of techniques known in the art for introducing cassettes and/or vectors into cells, for affecting the methods of the present invention, such as, but not limited to: direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation or liposome-mediated transfection, (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals).

In one embodiment, bombardment with nucleic acid coated particles may be a method for transferring a naked DNA expression construct into cells. This method depends on the ability to accelerate DNA-coated micro-projectiles to a high velocity allowing them to pierce cell membranes and enter cells without killing them. Several devices for accelerating small particles have been developed. One such device relies on a high voltage discharge to generate an electrical current, which in turn provides the motive force. The micro-projectiles used have comprised biologically inert or biocompatible substances such as tungsten or gold beads. It is to be understood that any of these methods may be utilized for introduction of the desired sequences into cells, and cells thereby produced are to be considered as part of this invention, as is their use for effecting the methods of this invention.

The efficacy of a particular expression vector system and method of introducing nucleic acid into a cell can be assessed by standard approaches routinely used in the art as described herein below.

Any one of a number of different vectors can be used, such as viral vectors, plasmid vectors, linear DNA, etc., as known in the art, to introduce an exogenous nucleic acid fragment encoding a peptide or protein or antibody or antibody binding fragment into target cells. These vectors can be inserted, for example, using infection, transduction, transfection, calcium-phosphate mediated transfection, DEAE-dextran mediated transfection, electroporation, liposome-mediated transfection, biolistic gene delivery, liposomal gene delivery using fusogenic and anionic liposomes (which are an alternative to the use of cationic liposomes), direct injection, receptor-mediated uptake, magnetoporation, ultrasound, or any combination thereof, as well as other techniques known in the art (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). The polynucleotide segments encoding sequences of interest can be ligated into an expression vector system suitable for transducing mammalian cells and for directing the expression of recombinant products within the transduced cells. Once the exogenous nucleic acid fragment has been incorporated into the cells using any of the techniques described above or known in the art, the production and/or the secretion rate of the therapeutic agent encoded by the nucleic acid fragment can be quantified. In one embodiment, the term "exogenous" refers to a substance that originated outside, for example a nucleic acid that originated outside of a cell or tissue.

In one embodiment, this invention provides a host cell transfected with a vector of this invention. In one embodiment the host cell may be a prokaryotic or eukaryotic cell. In one embodiment, the prokaryotic cell may be a bacterial cell. In one embodiment, the eukaryotic cell may be a fungal cell, a plant cell or an animal cell. In one embodiment, an animal cell is a human cell.

In one embodiment, nucleic acids of this invention are comprised in a vector. In one embodiment, a nucleic acid of this invention encodes a peptide or antibody or antibody binding fragment thereof of the current invention. In another embodiment a nucleic acid of this invention encodes a fragment of the peptide or antibody or antibody binding fragment thereof of the current invention. In yet another embodiment, a nucleic acid encodes a full length peptide or antibody or antibody binding fragment thereof of the current invention which further comprises a tag element. In some embodiments, the vector of and for use in a method of the present invention comprise a nucleic acid sequence operably linked to one or more regulatory sequences, wherein said nucleic acid sequence encodes peptide or antibody or antibody binding fragment thereof of the current invention. In another embodiment, the vector consists essentially of such a nucleic acid sequence, and in another embodiment, the vector consists of such a nucleic acid sequence.

Pharmaceutical Composition

Another aspect of the present invention relates to a pharmaceutical composition including a pharmaceutically acceptable carrier and an active ingredient. The phrase "active ingredient" refers to any of the peptides, the complex, conjugate or chimera, the functionally equivalent molecule that mimics the functional activity of the peptide, the conjugate, chimera or complex comprising the same, or a polynucleotide encoding the peptide or the complex according to the embodiments of the present invention. The pharmaceutical composition can contain one or more of the above-identified active ingredients of the present invention. Typically, the pharmaceutical composition of the present invention will include an active ingredient of the present invention, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of an active ingredient, together with the adjuvants, carriers and/or excipients. While individual needs may vary, determination of optimal ranges of effective amounts of each active ingredient, is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the active ingredient thereof of the present invention, can also be determined readily by those with ordinary skill in art. That is, the frequency of administration and size of the dose can be established by routine optimization, preferably while minimizing any side effects.

The solid unit dosage forms can be of the conventional type. The solid form can be a capsule and the like, such as an ordinary gelatin type containing the active ingredient thereof of the present invention, and a carrier, for example, lubricants and inert fillers such as, lactose, sucrose, or cornstarch. In another embodiment, the active ingredient is tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate. The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, the active ingredient can be incorporated with excipients and used in the form of tablets, capsules, elixirs, suspensions, syrups, and the like. Such compositions and preparations should contain at least 0.1% of active ingredient thereof. The percentage of the compound in these compositions can, of course, be varied and can conveniently be between about 2% to about 60% of the weight of the unit. The amount of active ingredient thereof in such therapeutically useful compositions is such that a suitable dosage will be obtained. Preferred compositions according to the present invention are prepared so that an oral dosage unit contains between about 1 mg and 800 mg of active ingredient thereof.

The active ingredient of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The active ingredient thereof or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

This active ingredient may be administered parenterally. Solutions or suspensions of these active ingredients thereof can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the active ingredient thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

When administering the active ingredient of the present invention, and pharmaceutical compositions thereof, they can be administered systemically or, alternatively, they can be administered directly to a specific site. Thus, administering can be accomplished in any manner effective for delivering the active ingredients thereof or the pharmaceutical compositions to the specific targeted cells. Exemplary modes of administration include, without limitation, administering the active ingredients thereof or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Determination of a therapeutically effective amount of an active ingredient peptide is well within the capability of those skilled in the art, especially in light of the detailed disclosure provided herein.

Toxicity and therapeutic efficacy of the peptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, for example, Fingl et al., 1975, in The Pharmacological Basis of Therapeutics, Ch. 1 p.1, the contents of which are hereby incorporated by reference in their entirety).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, depend on the subject being treated, the severity of the affliction, the manner of administration, the judgment of the prescribing physician, and all other relevant factors. Determination of the exact dose to be administered is conducted by methods known to a person of skill in the art.

It is further understood that the active ingredient of the invention can be formulated or administered together with additional active ingredients as required to treat the condition of the patient.

Method of Treating

In some embodiments of the invention, there is provided a method of treating cancer comprising the step of administering a therapeutically effective amount of: a complex comprising a peptide comprising the amino acid sequence set forth in WILVRLW (SEQ ID NO: 1), or any functionally related variant thereof, wherein the peptide is linked to a linker and wherein the linker is linked to RING; or a conjugate comprising a peptide comprising the amino acid sequence set forth in WILVRLW (SEQ ID NO: 1), or of any of the functionally related variants thereof, linked with or without a linker, to a small molecule or a peptide that recruits E3 ligase; or a conjugate comprising a functionally equivalent molecule that mimics a functional activity of the peptide comprising the amino acid sequence set forth in WILVRLW (SEQ ID NO: 1), or of any of the functionally related variants thereof, wherein the molecule is a peptidomimetic, a stapled peptide, or a chemical compound, and wherein the functionally equivalent molecule is linked with or without a linker to a small molecule or a peptide that recruits E3 ligase thereby treating cancer.

In some embodiments of the invention, there is provided a method of suppressing tumor growth comprising the step of administering a therapeutically effective amount of the complex or the conjugate, as described herein, thereby suppressing tumor growth.

In some embodiments, the cancer is breast cancer, bone osteosarcoma or glioblastoma.

In some embodiments, the tumor is a breast tumor, a bone tumor or a brain tumor.

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

EXAMPLES

Research Hypotheses

The ubiquitination reaction in cells is a highly regulated process. The interaction between the ubiquitin ligase (E3) and its substrate must be highly specific. Therefore, there is need to identify a specific binding site for p105 in the KPC1 in order to develop tumor suppressive drugs.

Research Objective

Identification of the binding site of KPC1 with its ubiquitination substrate p105.

Experimental Procedures

Plasmids Construction cDNAs for expression in mammalian cells were generated by PCR and cloned into a pCAGGS expression vector. KPC1 species i-iii, v (FIGS. 1 and 1B), viii (FIGS. 2A and 2B) and xi-xx (FIGS. 3a and 3B), were amplified with primers flanked with EcoRI and XhoI. KPC1 species iv (FIGS. 1A and 1B), vii, ix and x (FIGS. 2A and 2B) were amplified with primers flanked with BamHI and XhoI.

Cultured Cells

HEK293T cells were grown at 37° C. and 5% $CO_2$ in DMEM supplemented with 10% fetal calf serum and antibiotics (penicillin-streptomycin).

Co-Immunoprecipitation (Co-IP)

HEK293T cells were transiently transfected with the various KPC1 species along with p105-HA using the j etPEI reagent. 48 hours after transfection, the cells were harvested and lysed with RIPA buffer [150 mM NaCl, 0.5% sodium deoxycholate, 50 mM Tris-HCl (pH 8.0), 0.1% SDS, and 1% NP-40, supplemented with freshly added protease inhibitors mixture]. KPC1 species proteins were immunoprecipitated with immobilized anti-FLAG, with subsequent washing of the beads five times with RIPA buffer. The immunoprecipitated proteins were resolved by SDS-PAGE (10%, FIGS. 1A, 1B, 2A and 2B, with a gel gradient, of 4-20%; FIGS. 3A and 3B), and blotted onto nitrocellulose (FIGS. 1A, 1B, 2A and 2B) or PVDF (FIGS. 3A and 3B) membranes. p105 and KPC1 species were visualized using anti-NF-κB1 or anti-FLAG antibodies, respectively.

Example 1

Figure 1A:
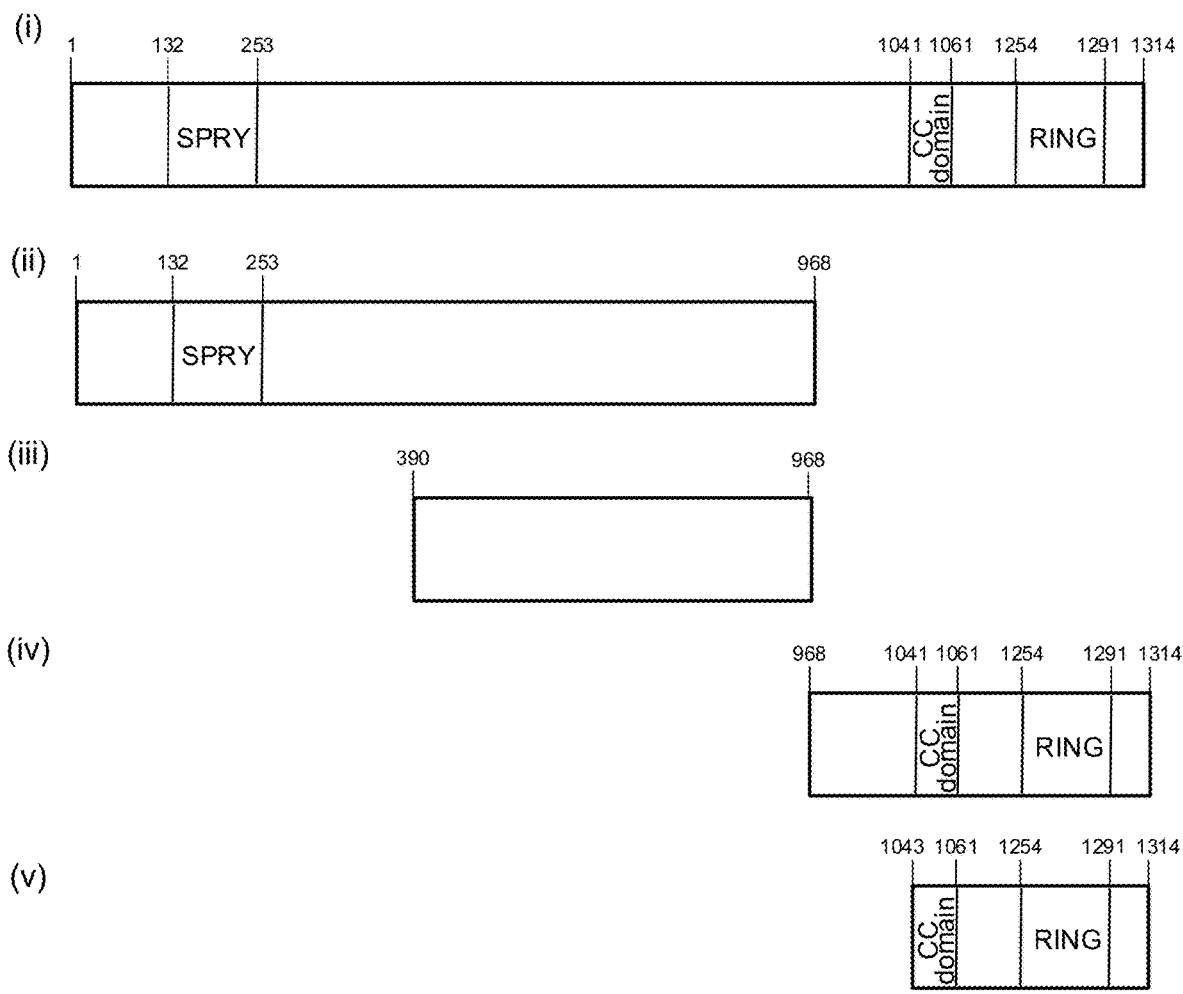
FIGS. 1A and 1B.
Figure 1B:
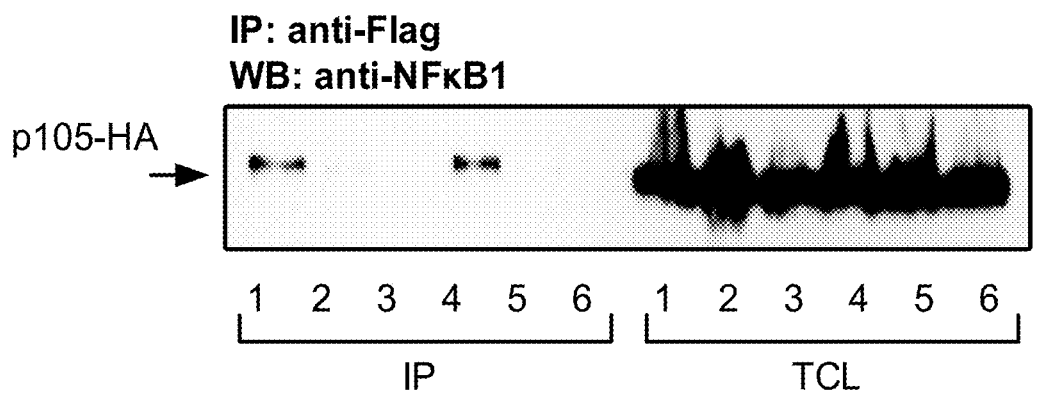
Figure 1B:
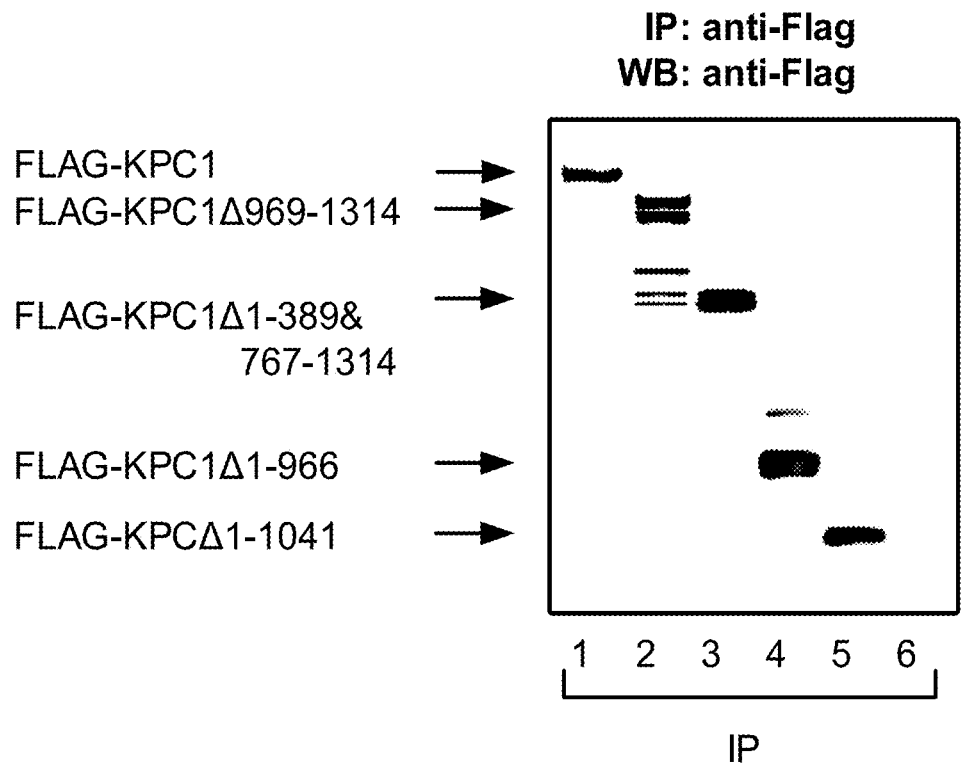
Figure 2A:
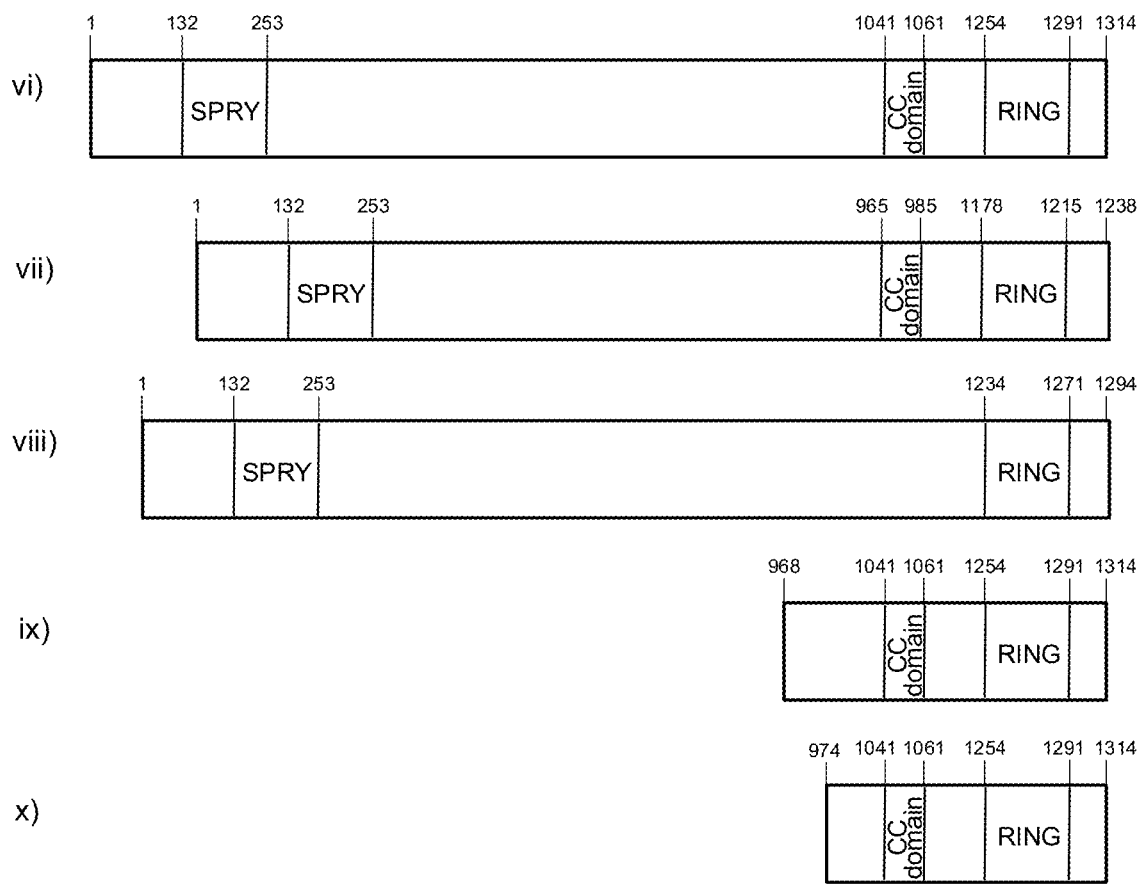
FIGS. 2A and 2B.
Figure 2B:
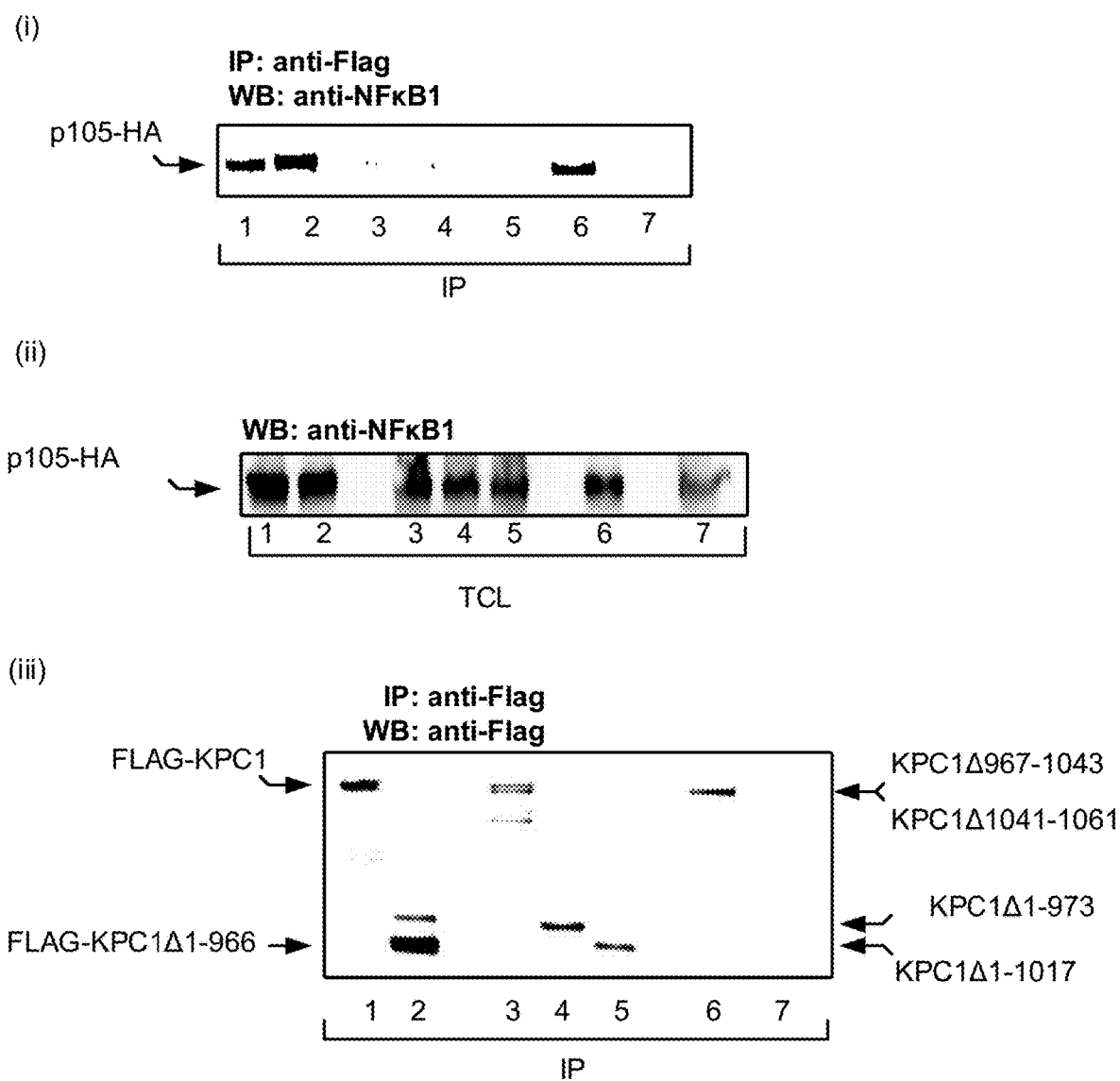

Identification of the region of KPC1 that is responsible for the interaction with p105. In order to identify the region of KPC1 that is responsible for the interaction with p105, several truncated segments of the DNA sequence of the KPC1 protein were cloned. The truncated segments were inserted into the pCAGGS expression vector to analyze their interaction with p105 by co-immunoprecipitation (Co-IP) from cells. HEK 293T cells were transfected with cDNAs coding for p105-HA, along with different fragments of KPC1 (FIG. 1A). Species of KPC1 were immunoprecipitated using an immobilized anti-Flag antibody. The precipitated proteins were resolved via SDS-PAGE and detected by Western blot using anti NF-κB1 and anti-FLAG antibodies.

In this IP experiment, an interaction between p105 and the full-length KPC1 protein was observed, as had already been shown in previous work in the inventors' laboratory. In addition, an interaction was observed between p105 and KPC1Δ1-967, indicating that the interaction occurs in the region downstream to amino acid 967 of KPC1. Indeed, when KPC1Δ1-1042 species was used for the IP, the interaction between these two proteins was abrogated. In order to narrow down the region of KPC1 that is responsible for the interaction with p105, additional four truncated species of KPC1 (FIG. 2A) were cloned, and their interaction with p105 was analyzed by co-immunoprecipitation (Co-IP) method (FIG. 2B).

An interaction between p105 and with both full-length KPC1 and KPC1ΔCC, as well as with KPC1Δ1-967. However, when KPC1Δ1-973 was used for IP, the interaction between these two proteins was abrogated, indicating that the domain necessary for interaction is located between amino acids 968-974. KPC1 truncated species KPC1Δ967-1043 and KPC1Δ1-1017 did not interact with p105.

In order to further narrow down the region of KPC1 that is responsible for the interaction with p105, another ten fragments of KPC1 were cloned (FIG. 3A). Then, their interaction with p105 by Co-IP was analyzed (FIG. 3B). Those ten truncated species of KPC1 contained only the last sixty amino acids of KPC1. In addition, various combinations containing seven or less amino acid residues (968-974) were cloned into the N-terminus, to more specifically determine which amino acid residue(s) in this range are required for binding of KPC1 to p105. An interaction was observed between p105 and WILVRLW-KPC1Δ1-1253, i.e. WIL-VRLWCPICYAHPISAVFQPCGHKSCK-ACINQHLMNNKDCFFCKTTIVSVED WEKGANT-STTSSAA (SEQ ID. No. 8). None of the other KPC1-species (xii-xx) showed a significant interaction with p105-HA protein. Based on these results, it was concluded that the minimal region of KPC1 that is essential for interaction with p105 is amino acids 968-974.

Example 2

Ubiquitination of p105 by Purified KPC1 and Different Mutant Species of KPC1, which Lack or Contain the Binding Site to p105 in Cell-Free Conjugation Assay.

In order to assess if the interaction between two proteins leads to the conjugation of the substrate p105, ubiquitination reaction was performed in cell free system. The conjugation reaction was carried out in the presence of purified Ub, E1, E2, UbAl, ATP and KPC1—either wild-type or different mutant species. Samples were resolved via SDS-PAGE and the 35S-labeled p105 and its adducts were visualized using autoradiography. KPC1 truncated mutant that harbors 7 amino acids WILVRLW (SEQ ID. No. 1) was found to ubiquitinate p105 in dose dependent manner (FIG. 4A, lanes 2-4), whereas its mutated counterpart that is lacking this sequence failed to stimulate the reaction (FIG. 4A, lanes 5-7). In addition, the shorter versions of KPC1 in which the 7 amino acids sequence were brought closer to RING domain, the active site of the enzyme were prepared. Both truncated KPC1 proteins that harbor the 7 amino acid sequence, WILVRLW-KPC1-Δ1-1039 (SEQ ID. No. 6) and WILVRLW-KPC1-Δ1-1061 (SEQ ID. No. 7), modified p105 (FIG. 4B, lanes 7-10). Altogether, these results indicate that WILVRLW amino acid sequence is responsible for interaction between the ligase KPC1 and the substrate p105.

To further confirm that 7 amino acids WILVRLW of KPC1-Δ1-967 (SEQ ID. No. 5) are involved in the interaction with p105, an experiment was designed in which the binding of p105 to the ligase was competed with a synthetic peptides derived from KPC1. The 7 amino acids peptide WILVRLW (SEQ ID NO: 1) inhibited ubiquitination of p105 by KPC1-Δ1-967 (SEQ ID. No. 5) to a larger extent compared to the 6 amino acids ILVRLW (SEQ ID NO: 9) peptide, which lacks the first tryptophan, both in a system that contained peptides modified by N-terminal amidation and C-terminal acetylation (FIG. 5) and in a system with non-modified peptides (FIG. 6). This results further confirm that the 7 amino acids sequence in KPC1 provides the specificity of binding between the ligase and the substrate p105.

To demonstrate that the processing of p105 is dependent on the binding of the ligase KPC1 through the 7 amino acid sequence WILVRLW (SEQ ID. No. 1), an experiment was performed in which the involvement of KPC1 deleted species in the processing of p105 in cell free system was tested. It was demonstrated that KPC1-Δ1-967-6xHIS that has the sequence of WILVRLW (SEQ ID. No. 1) stimulates the processing of p105 by purified proteasome (FIG. 7, lanes 4-5). KPC1-Δ1-974-6xHIS deleted species that is lacking the 7 amino acids that are responsible for the binding to p105 could not stimulate processing (FIG. 7, lanes 6-7).

Example 3

Overexpression of WILVRLW-KPC1Δ1-1039 (SEQ ID NO: 6) Repressed Glioblastoma U87-MG Tumor Growth in Nude Mice in a Similar Manner as KPC1.

In the experiment, as shown in FIG. 8 (A, B and C) that was carried out in vivo in nude mice, it was revealed that overexpression of WILVRLW-KPC1Δ1-1039 (SEQ ID NO: 6) in U87-MG cells injected to the mice repressed glioblastoma U87-MG tumor growth in the similar manner as overexpression of KPC1 in the U87-MG cells indicating that the truncated species mimics the function of the wild type protein almost completely.

Growth rates and weights (FIG. 8B) of tumor xenografts grown in nude mice, and derived from U87-MG expressing VO (control), Myc-KPC1, and Flag-WILVRLW-KPC1Δ1-1039 (SEQ ID. No. 6). FIG. 8C shows tumors derived from U87MG cells that stably express WILVRLW-KPC1Δ1-1039 (SEQ ID. No. 6) three weeks after inoculation.

REFERENCES

Glickman, M. H., and Ciechanover, A. (2002). The ubiquitin-proteasome proteolytic pathway: destruction for the sake of construction. Physiol. Rev. 82, 373-428. Kravtsova-Ivantsiv, Y., Shomer, I., Cohen-Kaplan, V., Snijder, B., Superti-Furga, G., Gonen, H., Sommer, T., Ziv, T., Admon, A., Naroditsky, I., et al. (2015). KPC1-mediated ubiquitination and proteasomal processing of NF-κB1 p105 to p50 restricts tumor growth. Cell 161, 333-347.

What is claimed is:

1. A peptide comprising the amino acid sequence set forth in WILVRLW (SEQ ID NO: 1), or any functionally related variant having at least 75% identity with the amino acid sequence set forth in SEQ ID NO: 1, wherein the peptide is less than 40 amino acids, and wherein said peptide or said functionally related variant interact with NF-κB p105.

2. The peptide according to claim 1, wherein said peptide comprises the sequence of amino acid residues positions 968-974 of the KIPI Ubiquitination Promoting Complex 1 (KPC1) protein set forth in SEQ ID NO: 2.

3. The peptide according to claim 1, wherein the functionally related variant of the amino acid sequence set forth in SEQ ID NO: 1, is a derivative having an N-terminal amidation and/or a C-terminal acetylation.

4. The peptide according to claim 1, wherein the functionally related variant of the amino acid sequence set forth in SEQ ID NO: 1, comprises substitution, deletion, and/or insertion at one position in WILVRLW (SEQ ID NO: 1).

5. The peptide according to claim 1, wherein the functionally related variant of the amino acid sequence set forth in SEQ ID NO: 1, has at least 85% sequence identity to the amino acid sequence set forth in WILVRLW (SEQ ID NO: 1).

6. A peptide having at least 95% identity to the peptide of claim 1.

7. A pharmaceutical composition comprising a therapeutically effective amount of peptide according to claim 1 and a pharmaceutically acceptable carrier or excipient.

8. A complex comprising the peptide of claim 1, wherein the peptide is linked to a linker and wherein the linker is linked to Really Interesting New Gene (RING), wherein the RING is CX2CX (9-39) CX (1-3) HX (2-3) C/HX2CX (4-48) CX2C with eight cysteines and histidines in a "cross-brace" topology to coordinate two zinc ions.

9. A conjugate comprising the peptide of claim 1, or any of the functionally related variants thereof; and a molecule or peptide that recruits E3 ligase.

10. An isolated polynucleotide encoding a peptide according to claim 1.

11. A method of treating cancer comprising the step of administering a therapeutically effective amount of:
a complex comprising a peptide of claim 1, wherein the peptide is linked to a linker and wherein the linker is linked to RING, wherein the RING is CX2CX (9-39) CX (1-3) HX (2-3)C/HX2CX (4-48) CX2C with eight cysteines and histidines in a "cross-brace" topology to coordinate two zinc ions; or
a conjugate comprising a peptide of claim 1, linked with or without a linker, to a small molecule or a peptide that recruits E3 ligase; wherein said peptide interacts with NF-κB p105; thereby treating cancer.

12. A peptide comprising the amino acid sequence set forth in WILVRLW (SEQ ID NO: 1), or any functionally related variant having at least 75% identity with the amino acid sequence set forth in SEQ ID NO: 1, wherein the peptide is less than 80 amino acids, and wherein said peptide or said functionally related variant interact with NF-κB p105.

13. A peptide comprising the amino acid sequence set forth in WILVRLW (SEQ ID NO: 1), or any functionally related variant having at least 75% identity with the amino acid sequence set forth in SEQ ID NO: 1, wherein the peptide is less than 60 amino acids, and wherein said peptide or said functionally related variant interact with NF-κB p105.

14. The complex according to claim 8, wherein said complex comprises the amino acid sequence as denoted in SEQ ID NO: 5, 6, or 7.

15. The conjugate according to claim 9, comprising the peptide of SEQ ID NO: 1, linked with or without a linker to a small molecule that recruits E3 ligase, wherein said small molecule is derived from lenalidomide.

16. The conjugate according to claim 15, comprising the peptide of SEQ ID NO: 1, linked with a liner to a small molecule derived from lenalidomide, said conjugate being:

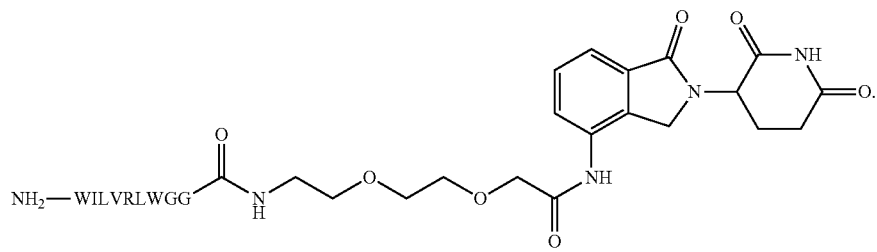
17. The peptide according to claim 1, wherein the peptide is less than 20 amino acids.
18. The peptide according to claim 1, wherein the peptide is 7 to 20 amino acids.
19. The peptide according to claim 1, comprising the amino acid sequence of SEQ ID NO: 1.
* * * * *

SEQUENCE LISTING

```
<160> NUMBER OF SEQ ID NOS: 22

<210> SEQ ID NO 1
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 1

Trp Ile Leu Val Arg Leu Trp
1               5

<210> SEQ ID NO 2
<211> LENGTH: 1314
<212> TYPE: PRT
<213> ORGANISM: Artificial Sequence
<220> FEATURE:
<223> OTHER INFORMATION: Synthetic Sequence

<400> SEQUENCE: 2

Met Ala Ser Lys Gly Ala Gly Met Ser Phe Ser Arg Lys Ser Tyr Arg
1               5                   10                  15

Leu Thr Ser Asp Ala Glu Lys Ser Arg Val Thr Gly Ile Val Gln Glu
                20                  25                  30

Lys Leu Leu Asn Asp Tyr Leu Asn Arg Ile Phe Ser Ser Ser Glu His
            35                  40                  45

Ala Pro Pro Ala Ala Thr Ser Arg Lys Pro Leu Asn Phe Gln Asn Leu
        50                  55                  60

Pro Glu His Leu Asp Gln Leu Leu Gln Val Asp Asn Glu Glu Glu Glu
65                  70                  75                  80

Ser Gln Gly Gln Val Glu Gly Arg Leu Gly Pro Ser Thr Val Val Leu
                85                  90                  95

Asp His Thr Gly Gly Phe Glu Gly Leu Leu Leu Val Asp Asp Asp Leu
                100                 105                 110

Leu Gly Val Ile Gly His Ser Asn Phe Gly Thr Ile Arg Ser Thr Thr
            115                 120                 125

Cys Val Tyr Lys Gly Lys Trp Leu Tyr Glu Val Leu Ile Ser Ser Gln
        130                 135                 140

Gly Leu Met Gln Ile Gly Trp Cys Thr Ile Ser Cys Arg Phe Asn Gln
145                 150                 155                 160

Glu Glu Gly Val Gly Asp Thr His Asn Ser Tyr Ala Tyr Asp Gly Asn
                165                 170                 175

Arg Val Arg Lys Trp Asn Val Thr Thr Thr Asn Tyr Gly Lys Ala Trp
                180                 185                 190

Ala Ala Gly Asp Ile Val Ser Cys Leu Ile Asp Leu Asp Asp Gly Thr
            195                 200                 205

Leu Ser Phe Cys Leu Asn Gly Val Ser Leu Gly Thr Ala Phe Glu Asn
        210                 215                 220

Leu Ser Arg Gly Leu Gly Met Ala Tyr Phe Pro Ala Ile Ser Leu Ser
225                 230                 235                 240

Phe Lys Glu Ser Val Ala Phe Asn Phe Gly Ser Arg Pro Leu Arg Tyr
                245                 250                 255

Pro Val Ala Gly Tyr Arg Pro Leu Gln Asp Pro Pro Ser Ala Asp Leu
```

-continued

```
            260                 265                 270
Val Arg Ala Gln Arg Leu Leu Gly Cys Phe Arg Ala Val Leu Ser Val
            275                 280                 285

Glu Leu Asp Pro Val Glu Gly Arg Leu Leu Asp Lys Glu Ser Ser Lys
            290                 295                 300

Trp Arg Leu Arg Gly Gln Pro Thr Val Leu Thr Leu Ala His Ile
305                 310                 315                 320

Phe His His Phe Ala Pro Leu Leu Arg Lys Val Tyr Leu Val Glu Ala
                    325                 330                 335

Val Leu Met Ser Phe Leu Leu Gly Ile Val Glu Lys Gly Thr Pro Thr
                340                 345                 350

Gln Ala Gln Ser Val Val His Gln Val Leu Asp Leu Leu Trp Leu Phe
                355                 360                 365

Met Glu Asp Tyr Glu Val Gln Asp Cys Leu Lys Gln Leu Met Met Ser
            370                 375                 380

Leu Leu Arg Leu Tyr Arg Phe Ser Pro Ile Val Pro Asp Leu Gly Leu
385                 390                 395                 400

Gln Ile His Tyr Leu Arg Leu Thr Ile Ala Ile Leu Arg His Glu Lys
                    405                 410                 415

Ser Arg Lys Phe Leu Leu Ser Asn Val Leu Phe Asp Val Leu Arg Ser
                420                 425                 430

Val Val Phe Phe Tyr Ile Lys Ser Pro Leu Arg Val Glu Glu Ala Gly
                435                 440                 445

Leu Gln Glu Leu Ile Pro Thr Thr Trp Trp Pro His Cys Ser Ser Arg
450                 455                 460

Glu Gly Lys Glu Ser Thr Glu Met Lys Glu Glu Thr Ala Glu Glu Arg
465                 470                 475                 480

Leu Arg Arg Arg Ala Tyr Glu Arg Gly Cys Gln Arg Leu Arg Lys Arg
                    485                 490                 495

Ile Glu Val Val Glu Glu Leu Gln Val Gln Ile Leu Lys Leu Leu Leu
                500                 505                 510

Asp Asn Lys Asp Asp Asn Gly Gly Glu Ala Ser Arg Tyr Ile Phe Leu
            515                 520                 525

Thr Lys Phe Arg Lys Phe Leu Gln Glu Asn Ala Ser Gly Arg Gly Asn
            530                 535                 540

Met Pro Met Leu Cys Pro Pro Glu Tyr Met Val Cys Phe Leu His Arg
545                 550                 555                 560

Leu Ile Ser Ala Leu Arg Tyr Tyr Trp Asp Glu Tyr Lys Ala Ser Asn
                565                 570                 575

Pro His Ala Ser Phe Ser Glu Glu Ala Tyr Ile Pro Pro Gln Val Phe
            580                 585                 590

Tyr Asn Gly Lys Val Asp Tyr Phe Asp Leu Gln Arg Leu Gly Gly Leu
            595                 600                 605

Leu Ser His Leu Arg Lys Thr Leu Lys Asp Asp Leu Ala Ser Lys Ala
            610                 615                 620

Asn Ile Val Ile Asp Pro Leu Glu Leu Gln Ser Thr Ala Met Asp Asp
625                 630                 635                 640

Leu Asp Glu Asp Glu Glu Pro Ala Pro Ala Met Ala Gln Arg Pro Met
                    645                 650                 655

Gln Ala Leu Ala Val Gly Gly Pro Leu Pro Leu Pro Arg Pro Gly Trp
                660                 665                 670

Leu Ser Ser Pro Thr Leu Gly Arg Ala Asn Arg Phe Leu Ser Thr Ala
            675                 680                 685
```

```
Ala Val Ser Leu Met Thr Pro Arg Arg Pro Leu Ser Thr Glu Lys
    690                 695                 700

Val Lys Val Arg Thr Leu Ser Val Glu Gln Arg Thr Arg Glu Asp Ile
705                 710                 715                 720

Glu Gly Ser His Trp Asn Glu Gly Leu Leu Gly Arg Pro Pro Glu
                725                 730                 735

Glu Pro Glu Gln Pro Leu Thr Glu Asn Ser Leu Leu Glu Val Leu Asp
            740                 745                 750

Gly Ala Val Met Met Tyr Asn Leu Ser Val His Gln Leu Gly Lys
            755                 760                 765

Met Val Gly Val Ser Asp Val Asn Glu Tyr Ala Met Ala Leu Arg
770                 775                 780

Asp Thr Glu Asp Lys Leu Arg Arg Cys Pro Lys Arg Arg Lys Asp Ile
785                 790                 795                 800

Leu Ala Glu Leu Thr Lys Ser Gln Lys Val Phe Ser Glu Lys Leu Asp
                805                 810                 815

His Leu Ser Arg Arg Leu Ala Trp Val His Ala Thr Val Tyr Ser Gln
                820                 825                 830

Glu Lys Met Leu Asp Ile Tyr Trp Leu Leu Arg Val Cys Leu Arg Thr
            835                 840                 845

Ile Glu His Gly Asp Arg Thr Gly Ser Leu Phe Ala Phe Met Pro Glu
850                 855                 860

Phe Tyr Leu Ser Val Ala Ile Asn Ser Tyr Ser Ala Leu Lys Asn Tyr
865                 870                 875                 880

Phe Gly Pro Val His Ser Met Glu Glu Leu Pro Gly Tyr Glu Glu Thr
                885                 890                 895

Leu Thr Arg Leu Ala Ala Ile Leu Ala Lys His Phe Ala Asp Ala Arg
                900                 905                 910

Ile Val Gly Thr Asp Ile Arg Asp Ser Leu Met Gln Ala Leu Ala Ser
            915                 920                 925

Tyr Val Cys Tyr Pro His Ser Leu Arg Ala Val Glu Arg Ile Pro Glu
            930                 935                 940

Glu Gln Arg Ile Ala Met Val Arg Asn Leu Leu Ala Pro Tyr Glu Gln
945                 950                 955                 960

Arg Pro Trp Ala Gln Thr Asn Trp Ile Leu Val Arg Leu Trp Arg Gly
                965                 970                 975

Cys Gly Phe Gly Tyr Arg Tyr Thr Arg Leu Pro His Leu Leu Lys Thr
            980                 985                 990

Lys Leu Glu Asp Ala Asn Leu Pro Ser Leu Gln Lys Pro Cys Pro Ser
            995                 1000                1005

Thr Leu Leu Gln Gln His Met Ala Asp Leu Leu Gln Gln Gly Pro
    1010                1015                1020

Asp Val Ala Pro Ser Phe Leu Asn Ser Val Leu Asn Gln Leu Asn
    1025                1030                1035

Trp Ala Phe Ser Glu Phe Ile Gly Met Ile Gln Glu Ile Gln Gln
    1040                1045                1050

Ala Ala Glu Arg Leu Glu Arg Asn Phe Val Asp Ser Arg Gln Leu
    1055                1060                1065

Lys Val Cys Ala Thr Cys Phe Asp Leu Ser Val Ser Leu Leu Arg
    1070                1075                1080

Val Leu Glu Met Thr Ile Thr Leu Val Pro Glu Ile Phe Leu Asp
    1085                1090                1095
```

Trp Thr Arg Pro Thr Ser Glu Met Leu Leu Arg Arg Leu Ala Gln
1100                1105                1110

Leu Leu Asn Gln Val Leu Asn Arg Val Thr Ala Glu Arg Asn Leu
    1115                1120                1125

Phe Asp Arg Val Val Thr Leu Arg Leu Pro Gly Leu Glu Ser Val
1130                1135                1140

Asp His Tyr Pro Ile Leu Val Ala Val Thr Gly Ile Leu Val Gln
    1145                1150                1155

Leu Leu Val Arg Gly Pro Ala Ser Glu Arg Glu Gln Ala Thr Ser
1160                1165                1170

Val Leu Leu Ala Asp Pro Cys Phe Gln Leu Arg Ser Ile Cys Tyr
    1175                1180                1185

Leu Leu Gly Gln Pro Glu Pro Pro Ala Pro Gly Thr Ala Leu Pro
1190                1195                1200

Ala Pro Asp Arg Lys Arg Phe Ser Leu Gln Ser Tyr Ala Asp Tyr
    1205                1210                1215

Ile Ser Ala Asp Glu Leu Ala Gln Val Glu Gln Met Leu Ala His
1220                1225                1230

Leu Thr Ser Ala Ser Ala Gln Ala Ala Ala Ser Leu Pro Thr
    1235                1240                1245

Ser Glu Glu Asp Leu Cys Pro Ile Cys Tyr Ala His Pro Ile Ser
1250                1255                1260

Ala Val Phe Gln Pro Cys Gly His Lys Ser Cys Lys Ala Cys Ile
    1265                1270                1275

Asn Gln His Leu Met Asn Asn Lys Asp Cys Phe Phe Cys Lys Thr
1280                1285                1290

Thr Ile Val Ser Val Glu Asp Trp Glu Lys Gly Ala Asn Thr Ser
    1295                1300                1305

Thr Thr Ser Ser Ala Ala
1310

<210> SEQ ID NO 3
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 3

Gly Gly Gly Gly Gly Gly
1               5

<210> SEQ ID NO 4
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 4

Cys Pro Ile Cys Tyr Ala His Pro Ile Ser Ala Val Phe Gln Pro Cys
1               5                   10                  15

Gly His Lys Ser Cys Lys Ala Cys Ile Asn Gln His Leu Met Asn Asn
            20                  25                  30

Lys Asp Cys Phe Phe Cys
        35

<210> SEQ ID NO 5

```
<211> LENGTH: 347
<212> TYPE: PRT
<213> ORGANISM: Artificial Sequence
<220> FEATURE:
<223> OTHER INFORMATION: synthetic sequence

<400> SEQUENCE: 5

Trp Ile Leu Val Arg Leu Trp Arg Gly Cys Gly Phe Gly Tyr Arg Tyr
1               5                   10                  15

Thr Arg Leu Pro His Leu Leu Lys Thr Lys Leu Glu Asp Ala Asn Leu
            20                  25                  30

Pro Ser Leu Gln Lys Pro Cys Pro Ser Thr Leu Leu Gln Gln His Met
        35                  40                  45

Ala Asp Leu Leu Gln Gln Gly Pro Asp Val Ala Pro Ser Phe Leu Asn
50                  55                  60

Ser Val Leu Asn Gln Leu Asn Trp Ala Phe Ser Glu Phe Ile Gly Met
65                  70                  75                  80

Ile Gln Glu Ile Gln Gln Ala Ala Glu Arg Leu Glu Arg Asn Phe Val
                85                  90                  95

Asp Ser Arg Gln Leu Lys Val Cys Ala Thr Cys Phe Asp Leu Ser Val
            100                 105                 110

Ser Leu Leu Arg Val Leu Glu Met Thr Ile Thr Leu Val Pro Glu Ile
        115                 120                 125

Phe Leu Asp Trp Thr Arg Pro Thr Ser Glu Met Leu Leu Arg Arg Leu
130                 135                 140

Ala Gln Leu Leu Asn Gln Val Leu Asn Arg Val Thr Ala Glu Arg Asn
145                 150                 155                 160

Leu Phe Asp Arg Val Val Thr Leu Arg Leu Pro Gly Leu Glu Ser Val
                165                 170                 175

Asp His Tyr Pro Ile Leu Val Ala Val Thr Gly Ile Leu Val Gln Leu
            180                 185                 190

Leu Val Arg Gly Pro Ala Ser Glu Arg Glu Gln Ala Thr Ser Val Leu
        195                 200                 205

Leu Ala Asp Pro Cys Phe Gln Leu Arg Ser Ile Cys Tyr Leu Leu Gly
210                 215                 220

Gln Pro Glu Pro Pro Ala Pro Gly Thr Ala Leu Pro Ala Pro Asp Arg
225                 230                 235                 240

Lys Arg Phe Ser Leu Gln Ser Tyr Ala Asp Tyr Ile Ser Ala Asp Glu
                245                 250                 255

Leu Ala Gln Val Glu Gln Met Leu Ala His Leu Thr Ser Ala Ser Ala
            260                 265                 270

Gln Ala Ala Ala Ser Leu Pro Thr Ser Glu Glu Asp Leu Cys Pro
        275                 280                 285

Ile Cys Tyr Ala His Pro Ile Ser Ala Val Phe Gln Pro Cys Gly His
290                 295                 300

Lys Ser Cys Lys Ala Cys Ile Asn Gln His Leu Met Asn Asn Lys Asp
305                 310                 315                 320

Cys Phe Phe Cys Lys Thr Thr Ile Val Ser Val Glu Asp Trp Glu Lys
                325                 330                 335

Gly Ala Asn Thr Ser Thr Thr Ser Ser Ala Ala
            340                 345

<210> SEQ ID NO 6
<211> LENGTH: 282
<212> TYPE: PRT
<213> ORGANISM: Artificial Sequence
```

<220> FEATURE:
<223> OTHER INFORMATION: synthetic sequence

<400> SEQUENCE: 6

```
Trp Ile Leu Val Arg Leu Trp Ala Phe Ser Glu Phe Ile Gly Met Ile
1               5                   10                  15

Gln Glu Ile Gln Gln Ala Ala Glu Arg Leu Glu Arg Asn Phe Val Asp
            20                  25                  30

Ser Arg Gln Leu Lys Val Cys Ala Thr Cys Phe Asp Leu Ser Val Ser
        35                  40                  45

Leu Leu Arg Val Leu Glu Met Thr Ile Thr Leu Val Pro Glu Ile Phe
    50                  55                  60

Leu Asp Trp Thr Arg Pro Thr Ser Glu Met Leu Leu Arg Arg Leu Ala
65                  70                  75                  80

Gln Leu Leu Asn Gln Val Leu Asn Arg Val Thr Ala Glu Arg Asn Leu
                85                  90                  95

Phe Asp Arg Val Val Thr Leu Arg Leu Pro Gly Leu Glu Ser Val Asp
            100                 105                 110

His Tyr Pro Ile Leu Val Ala Val Thr Gly Ile Leu Val Gln Leu Leu
        115                 120                 125

Val Arg Gly Pro Ala Ser Glu Arg Glu Gln Ala Thr Ser Val Leu Leu
    130                 135                 140

Ala Asp Pro Cys Phe Gln Leu Arg Ser Ile Cys Tyr Leu Leu Gly Gln
145                 150                 155                 160

Pro Glu Pro Pro Ala Pro Gly Thr Ala Leu Pro Ala Pro Asp Arg Lys
                165                 170                 175

Arg Phe Ser Leu Gln Ser Tyr Ala Asp Tyr Ile Ser Ala Asp Glu Leu
            180                 185                 190

Ala Gln Val Glu Gln Met Leu Ala His Leu Thr Ser Ala Ser Ala Gln
        195                 200                 205

Ala Ala Ala Ala Ser Leu Pro Thr Ser Glu Glu Asp Leu Cys Pro Ile
210                 215                 220

Cys Tyr Ala His Pro Ile Ser Ala Val Phe Gln Pro Cys Gly His Lys
225                 230                 235                 240

Ser Cys Lys Ala Cys Ile Asn Gln His Leu Met Asn Asn Lys Asp Cys
                245                 250                 255

Phe Phe Cys Lys Thr Thr Ile Ser Val Glu Asp Trp Glu Lys Gly
            260                 265                 270

Ala Asn Thr Ser Thr Thr Ser Ser Ala Ala
            275                 280
```

<210> SEQ ID NO 7
<211> LENGTH: 260
<212> TYPE: PRT
<213> ORGANISM: Artificial Sequence
<220> FEATURE:
<223> OTHER INFORMATION: synthetic sequence

<400> SEQUENCE: 7

```
Trp Ile Leu Val Arg Leu Trp Phe Val Asp Ser Arg Gln Leu Lys Val
1               5                   10                  15

Cys Ala Thr Cys Phe Asp Leu Ser Val Ser Leu Leu Arg Val Leu Glu
            20                  25                  30

Met Thr Ile Thr Leu Val Pro Glu Ile Phe Leu Asp Trp Thr Arg Pro
        35                  40                  45

Thr Ser Glu Met Leu Leu Arg Arg Leu Ala Gln Leu Leu Asn Gln Val
```

```
                50                  55                  60
Leu Asn Arg Val Thr Ala Glu Arg Asn Leu Phe Asp Arg Val Thr
 65                  70                  75                  80

Leu Arg Leu Pro Gly Leu Glu Ser Val Asp His Tyr Pro Ile Leu Val
                 85                  90                  95

Ala Val Thr Gly Ile Leu Val Gln Leu Val Arg Gly Pro Ala Ser
                100                 105                 110

Glu Arg Glu Gln Ala Thr Ser Val Leu Leu Ala Asp Pro Cys Phe Gln
                115                 120                 125

Leu Arg Ser Ile Cys Tyr Leu Leu Gly Gln Pro Glu Pro Pro Ala Pro
            130                 135                 140

Gly Thr Ala Leu Pro Ala Pro Asp Arg Lys Arg Phe Ser Leu Gln Ser
145                 150                 155                 160

Tyr Ala Asp Tyr Ile Ser Ala Asp Glu Leu Ala Gln Val Glu Gln Met
                165                 170                 175

Leu Ala His Leu Thr Ser Ala Ser Ala Gln Ala Ala Ala Ser Leu
                180                 185                 190

Pro Thr Ser Glu Glu Asp Leu Cys Pro Ile Cys Tyr Ala His Pro Ile
                195                 200                 205

Ser Ala Val Phe Gln Pro Cys Gly His Lys Ser Cys Lys Ala Cys Ile
            210                 215                 220

Asn Gln His Leu Met Asn Asn Lys Asp Cys Phe Phe Cys Lys Thr Thr
225                 230                 235                 240

Ile Val Ser Val Glu Asp Trp Glu Lys Gly Ala Asn Thr Ser Thr Thr
                245                 250                 255

Ser Ser Ala Ala
        260

<210> SEQ ID NO 8
<211> LENGTH: 68
<212> TYPE: PRT
<213> ORGANISM: Artificial Sequence
<220> FEATURE:
<223> OTHER INFORMATION: synthetic sequence

<400> SEQUENCE: 8

Trp Ile Leu Val Arg Leu Trp Cys Pro Ile Cys Tyr Ala His Pro Ile
 1               5                  10                  15

Ser Ala Val Phe Gln Pro Cys Gly His Lys Ser Cys Lys Ala Cys Ile
                20                  25                  30

Asn Gln His Leu Met Asn Asn Lys Asp Cys Phe Phe Cys Lys Thr Thr
            35                  40                  45

Ile Val Ser Val Glu Asp Trp Glu Lys Gly Ala Asn Thr Ser Thr Thr
        50                  55                  60

Ser Ser Ala Ala
65

<210> SEQ ID NO 9
<211> LENGTH: 6
<212> TYPE: PRT
<213> ORGANISM: Artificial Sequence
<220> FEATURE:
<223> OTHER INFORMATION: synthetic sequence

<400> SEQUENCE: 9

Ile Leu Val Arg Leu Trp
 1               5
```

<210> SEQ ID NO 10
<211> LENGTH: 67
<212> TYPE: PRT
<213> ORGANISM: Artificial Sequence
<220> FEATURE:
<223> OTHER INFORMATION: synthetic sequence

<400> SEQUENCE: 10

```
Ile Leu Val Arg Leu Trp Cys Pro Ile Cys Tyr Ala His Pro Ile Ser
1               5                   10                  15

Ala Val Phe Gln Pro Cys Gly His Lys Ser Cys Lys Ala Cys Ile Asn
            20                  25                  30

Gln His Leu Met Asn Asn Lys Asp Cys Phe Phe Cys Lys Thr Thr Ile
        35                  40                  45

Val Ser Val Glu Asp Trp Glu Lys Gly Ala Asn Thr Ser Thr Thr Ser
    50                  55                  60

Ser Ala Ala
65
```

<210> SEQ ID NO 11
<211> LENGTH: 66
<212> TYPE: PRT
<213> ORGANISM: Artificial Sequence
<220> FEATURE:
<223> OTHER INFORMATION: synthetic sequence

<400> SEQUENCE: 11

```
Leu Val Arg Leu Trp Cys Pro Ile Cys Tyr Ala His Pro Ile Ser Ala
1               5                   10                  15

Val Phe Gln Pro Cys Gly His Lys Ser Cys Lys Ala Cys Ile Asn Gln
            20                  25                  30

His Leu Met Asn Asn Lys Asp Cys Phe Phe Cys Lys Thr Thr Ile Val
        35                  40                  45

Ser Val Glu Asp Trp Glu Lys Gly Ala Asn Thr Ser Thr Thr Ser Ser
    50                  55                  60

Ala Ala
65
```

<210> SEQ ID NO 12
<211> LENGTH: 65
<212> TYPE: PRT
<213> ORGANISM: Artificial Sequence
<220> FEATURE:
<223> OTHER INFORMATION: synthetic sequence

<400> SEQUENCE: 12

```
Val Arg Leu Trp Cys Pro Ile Cys Tyr Ala His Pro Ile Ser Ala Val
1               5                   10                  15

Phe Gln Pro Cys Gly His Lys Ser Cys Lys Ala Cys Ile Asn Gln His
            20                  25                  30

Leu Met Asn Asn Lys Asp Cys Phe Phe Cys Lys Thr Thr Ile Val Ser
        35                  40                  45

Val Glu Asp Trp Glu Lys Gly Ala Asn Thr Ser Thr Thr Ser Ser Ala
    50                  55                  60

Ala
65
```

<210> SEQ ID NO 13
<211> LENGTH: 64
<212> TYPE: PRT

```
<213> ORGANISM: Artificial Sequence
<220> FEATURE:
<223> OTHER INFORMATION: synthetic sequence

<400> SEQUENCE: 13

Arg Leu Trp Cys Pro Ile Cys Tyr Ala His Pro Ile Ser Ala Val Phe
1               5                   10                  15

Gln Pro Cys Gly His Lys Ser Cys Lys Ala Cys Ile Asn Gln His Leu
            20                  25                  30

Met Asn Asn Lys Asp Cys Phe Phe Cys Lys Thr Thr Ile Val Ser Val
        35                  40                  45

Glu Asp Trp Glu Lys Gly Ala Asn Thr Ser Thr Ser Ser Ala Ala
    50                  55                  60

<210> SEQ ID NO 14
<211> LENGTH: 67
<212> TYPE: PRT
<213> ORGANISM: Artificial Sequence
<220> FEATURE:
<223> OTHER INFORMATION: synthetic sequence

<400> SEQUENCE: 14

Trp Ile Leu Val Arg Leu Cys Pro Ile Cys Tyr Ala His Pro Ile Ser
1               5                   10                  15

Ala Val Phe Gln Pro Cys Gly His Lys Ser Cys Lys Ala Cys Ile Asn
            20                  25                  30

Gln His Leu Met Asn Asn Lys Asp Cys Phe Phe Cys Lys Thr Thr Ile
        35                  40                  45

Val Ser Val Glu Asp Trp Glu Lys Gly Ala Asn Thr Ser Thr Thr Ser
    50                  55                  60

Ser Ala Ala
65

<210> SEQ ID NO 15
<211> LENGTH: 66
<212> TYPE: PRT
<213> ORGANISM: Artificial Sequence
<220> FEATURE:
<223> OTHER INFORMATION: synthetic sequence

<400> SEQUENCE: 15

Trp Ile Leu Val Arg Cys Pro Ile Cys Tyr Ala His Pro Ile Ser Ala
1               5                   10                  15

Val Phe Gln Pro Cys Gly His Lys Ser Cys Lys Ala Cys Ile Asn Gln
            20                  25                  30

His Leu Met Asn Asn Lys Asp Cys Phe Phe Cys Lys Thr Thr Ile Val
        35                  40                  45

Ser Val Glu Asp Trp Glu Lys Gly Ala Asn Thr Ser Thr Thr Ser Ser
    50                  55                  60

Ala Ala
65

<210> SEQ ID NO 16
<211> LENGTH: 65
<212> TYPE: PRT
<213> ORGANISM: Artificial Sequence
<220> FEATURE:
<223> OTHER INFORMATION: synthetic sequence

<400> SEQUENCE: 16

Trp Ile Leu Val Cys Pro Ile Cys Tyr Ala His Pro Ile Ser Ala Val
```

```
1               5                   10                  15
Phe Gln Pro Cys Gly His Lys Ser Cys Lys Ala Cys Ile Asn Gln His
            20                  25                  30

Leu Met Asn Asn Lys Asp Cys Phe Phe Cys Lys Thr Thr Ile Val Ser
        35                  40                  45

Val Glu Asp Trp Glu Lys Gly Ala Asn Thr Ser Thr Thr Ser Ser Ala
    50                  55                  60

Ala
65

<210> SEQ ID NO 17
<211> LENGTH: 64
<212> TYPE: PRT
<213> ORGANISM: Artificial Sequence
<220> FEATURE:
<223> OTHER INFORMATION: synthetic sequence

<400> SEQUENCE: 17

Trp Ile Leu Cys Pro Ile Cys Tyr Ala His Pro Ile Ser Ala Val Phe
1               5                   10                  15

Gln Pro Cys Gly His Lys Ser Cys Lys Ala Cys Ile Asn Gln His Leu
            20                  25                  30

Met Asn Asn Lys Asp Cys Phe Phe Cys Lys Thr Thr Ile Val Ser Val
        35                  40                  45

Glu Asp Trp Glu Lys Gly Ala Asn Thr Ser Thr Thr Ser Ser Ala Ala
    50                  55                  60

<210> SEQ ID NO 18
<211> LENGTH: 5
<212> TYPE: PRT
<213> ORGANISM: Artificial Sequence
<220> FEATURE:
<223> OTHER INFORMATION: synthetic sequence

<400> SEQUENCE: 18

Leu Val Arg Leu Trp
1               5

<210> SEQ ID NO 19
<211> LENGTH: 4
<212> TYPE: PRT
<213> ORGANISM: Artificial Sequence
<220> FEATURE:
<223> OTHER INFORMATION: synthetic sequence

<400> SEQUENCE: 19

Val Arg Leu Trp
1

<210> SEQ ID NO 20
<211> LENGTH: 6
<212> TYPE: PRT
<213> ORGANISM: Artificial Sequence
<220> FEATURE:
```

```
<223> OTHER INFORMATION: Synthetic Sequence

<400> SEQUENCE: 20

Trp Ile Leu Val Arg Leu
1               5

<210> SEQ ID NO 21
<211> LENGTH: 5
<212> TYPE: PRT
<213> ORGANISM: Artificial Sequence
<220> FEATURE:
<223> OTHER INFORMATION: synthetic sequence

<400> SEQUENCE: 21

Trp Ile Leu Val Arg
1               5

<210> SEQ ID NO 22
<211> LENGTH: 4
<212> TYPE: PRT
<213> ORGANISM: Artificial Sequence
<220> FEATURE:
<223> OTHER INFORMATION: synthetic sequence

<400> SEQUENCE: 22

Trp Ile Leu Val
1
```